United States Patent
Sugiyama et al.

(10) Patent No.: US 10,401,273 B2
(45) Date of Patent: Sep. 3, 2019

(54) PARTICLE DETECTION SYSTEM

(71) Applicant: NGK SPARK PLUG CO., LTD., Nagoya-shi, Aichi (JP)

(72) Inventors: Takeshi Sugiyama, Ichinomiya (JP); Masayuki Motomura, Komak (JP); Norimasa Osawa, Inuyama (JP); Hirokazu Murase, Nisshin (JP)

(73) Assignee: NGK SPARK PLUG CO., LTD., Nagoya-shi, Aichi (JP)

( * ) Notice: Subject to any disclaimer, the term of this patent is extended or adjusted under 35 U.S.C. 154(b) by 23 days.

(21) Appl. No.: 15/517,420

(22) PCT Filed: Oct. 13, 2015

(86) PCT No.: PCT/JP2015/005167
§ 371 (c)(1),
(2) Date: Apr. 6, 2017

(87) PCT Pub. No.: WO2016/063491
PCT Pub. Date: Apr. 28, 2016

(65) Prior Publication Data
US 2017/0307498 A1    Oct. 26, 2017

(30) Foreign Application Priority Data

Oct. 24, 2014  (JP) ................. 2014-217344

(51) Int. Cl.
*G01N 15/06*  (2006.01)
*G01M 15/10*  (2006.01)
(Continued)

(52) U.S. Cl.
CPC ............. *G01N 15/06* (2013.01); *F01N 11/00* (2013.01); *G01M 15/102* (2013.01);
(Continued)

(58) Field of Classification Search
CPC ...... G01N 15/06; G01N 27/60; G01M 15/102
(Continued)

(56) References Cited

U.S. PATENT DOCUMENTS

2011/0314796 A1* 12/2011 Nakamura ............. F01N 9/002
60/276
2012/0312074 A1   12/2012 Allmendiner et al.
(Continued)

FOREIGN PATENT DOCUMENTS

JP    59-197847 A    11/1984
JP    2003-98136 A    4/2003
(Continued)

OTHER PUBLICATIONS

Communication dated Mar. 27, 2018, from the Japanese Patent Office in counterpart application No. 2014-217344.
(Continued)

*Primary Examiner* — Natalie Huls
*Assistant Examiner* — Suman K Nath
(74) *Attorney, Agent, or Firm* — Sughrue Mion, PLLC

(57) ABSTRACT

A particle detection system (1) includes a particle sensor (10) having a detection section (11) exposed to a gas under measurement EG. The particle sensor (10) includes an insulating member (121, 100), and a heater section (150, 105) for heating at least a portion of the gas contact surface (121s, 101s) of the insulating member (121, 100). The particle detection system (1) includes adhesive restraining energization means (225, 223, S4, S10) for heating the gas contact surface (121s, 101s) to an adhesion restraining temperature Td at which adhesion of the particles S to the gas contact surface (121s, 101s) is restrained as compared with the case where the heater section is not energized,
(Continued)

wherein adhering particles SA which are particles adhering to the gas contact surface (121*s*, 101*s*) burn at the particle burning temperature Tb.

5 Claims, 12 Drawing Sheets

(51) Int. Cl.
*F01N 11/00* (2006.01)
*G01N 27/60* (2006.01)
*G01N 15/00* (2006.01)

(52) U.S. Cl.
CPC ......... *G01N 15/0656* (2013.01); *G01N 27/60* (2013.01); *F01N 2560/05* (2013.01); *F01N 2560/20* (2013.01); *G01N 2015/0046* (2013.01); *Y02T 10/47* (2013.01)

(58) Field of Classification Search
USPC .................. 73/23.2, 23.23, 28.01; 338/34; 204/424–431
See application file for complete search history.

(56) References Cited

U.S. PATENT DOCUMENTS

| | | |
|---|---|---|
| 2013/0219990 A1 | 8/2013 | Allmendinger et al. |
| 2014/0352405 A1 | 12/2014 | Motomura et al. |
| 2015/0204759 A1 | 7/2015 | Sugiyama et al. |

FOREIGN PATENT DOCUMENTS

| | | |
|---|---|---|
| JP | 2011-074809 A | 4/2011 |
| JP | 2011-080942 A | 4/2011 |
| JP | 2012-047722 A | 3/2012 |
| JP | 2013-170914 A | 9/2013 |
| JP | 2013-195069 A | 9/2013 |
| JP | 2013-238584 A | 11/2013 |
| WO | 2014-054390 A1 | 4/2014 |

OTHER PUBLICATIONS

International Search Report for PCT/JP2015/005167 dated Jan. 12, 2016 [PCT/ISA/210].

\* cited by examiner

PARTICLE DETECTION SYSTEM

CROSS REFERENCE TO RELATED APPLICATIONS

This application is a National Stage of International Application No. PCT/JP2015/005167 filed Oct 13, 2015, claiming priority based on Japanese Patent Application No. 2014-217344 filed Oct 24, 2014, the contents of all of which are incorporated herein by reference in their entirety.

TECHNICAL FIELD

The present invention relates to a particle detection system for detecting particles contained in a gas under measurement.

BACKGROUND ART

Conventionally, there has been known a particle detection system which includes a particle sensor for detecting particles such as soot contained in a gas under measurement. A specific example of such a particle detection system is a particle detection system which produces ions by means of corona discharge, and electrifies particles (soot, etc.) contained in exhaust gas through use of the produced ions, to thereby detect the amount of particles contained in the exhaust gas. As an example of such a particle detection system, Patent Document 1 discloses a particle detection system which is mounted on a vehicle having a diesel engine and in which a particle sensor 100 and a sensor drive section 110 for controlling the same are connected through a cable 120.

Also, Patent Documents 2 and 3 disclose a particle detection system whose detection section includes a pair of electrodes overlapping each other to form the shape of a double-wall tube and in which, after PM agglomerates (PM structures (particulate matter structures)); i.e., particles adhering to the surface of an electrode, are previously formed through use of particles contained in a gas under measurement flowing through the space between the electrodes, the gas under measurement is caused to flow through the space between the electrodes, and a high voltage is applied between the electrodes. Thus, electrified PM agglomerates move between the electrodes, and the particles are detected through use of the electrified PM agglomerates.

In these particle detection systems, when particles such as soot adhere to the surface of an insulating member provided in a particle sensor and deteriorate the insulation performance of the insulating member at the surface, the detection performance may deteriorate; for example, the particle detection accuracy may lower or the detection may become impossible. In order to overcome such a problem, there has been proposed a particle detection system in which its particle sensor has a heater for heating the surface of the insulating member, and particles such as soot adhering to the surface of the insulating member are burned and removed by heating by the heater. For example, in the particle detection system of Patent Document 1, a heater pattern 380 is provided in a sensor unit 300 formed of an insulating ceramic (insulating material) and provided in the particle sensor 100. This heater pattern 380 heats the entirety of the sensor unit 300 to 550 to 600° C. to thereby burn soot adhering to a first electrode 322 of a discharge pattern 320, etc.

PRIOR ART DOCUMENTS

Patent Documents

Patent Document 1: Japanese Patent Application Laid-Open (kokai) No. 2013-170914
Patent Document 2: United States Patent Application Laid-Open (kokai) No. US2012/0312074A1
Patent Document 3: United States Patent Application Laid-Open (kokai) No. US2013/0219990A1

SUMMARY OF THE INVENTION

Problem to be Solved by the Invention

Incidentally, it has been gradually revealed that when the insulating member of a particle sensor is heated to a temperature which is equal to or higher than a predetermined temperature but is lower than a temperature for burning particles such as soot adhering to the surface of the insulating member, particles become less likely to adhere to the surface of the insulating member.

The present invention has been accomplished in view of such a finding, and its object is to provide a particle detection system which can restrain adhesion of particles to the surface of an insulating member of a particle sensor.

Means for Solving the Problem

One mode of the present invention is a particle detection system comprising a particle sensor which has a detection section to be exposed to a gas under measurement and which detects particles contained in the gas under measurement, wherein the particle sensor includes: an insulating member formed of an insulating material having a gas contact surface which comes into contact with the gas under measurement and whose insulating performance deteriorates when the particles contained in the gas under measurement adhere thereto, to thereby lower a performance of detecting the particles by the detection section, and a heater section which generates heat upon energization so as to heat at least a portion of the gas contact surface of the insulating member; and the particle detection system comprises adhesion restraining energization means for heating the gas contact surface, by energization of the heater section, to an adhesion restraining temperature which is lower than a particle burning temperature but at which adhesion of the particles to the gas contact surface is restrained as compared with the case where the heater section is not energized, wherein adhering particles which are particles adhering to the gas contact surface burn at the particle burning temperature.

In this particle detection system, through energization of the heater section by the adhesion restraining energization means, the gas contact surface of the insulating member is heated to the adhesion restraining temperature (the adhesion restraining temperature is lower than the particle burning temperature at which adhering particles; i.e., particles adhering to the gas contact surface of the insulating member burn, but at the adhesion restraining temperature, adhesion of the particles to the gas contact surface is restrained as compared with the case where the heater section is not energized). As a result, as compared with the case where the heater section is not energized, adhesion of the particles to the gas contact surface can be restrained.

Notably, the particle burning temperature at which the adhering particles such as soot burn is, for example, a temperature which falls within a temperature range of 650°

C. to 700° C. or higher. Meanwhile, the adhesion restraining temperature is a temperature which is lower than the particle burning temperature and at which adhesion of particles to the gas contact surface is restrained. More specifically, the adhesion restraining temperature is, for example, a temperature selected from a temperature range which ranges from a temperature higher than the temperature of the gas under measurement by about several tens to one hundred degrees Celsius to the lowest particle burning temperature at which the adhering particles burn. Although the temperature of exhaust gas which is the gas under measurement changes depending on the type of the engine, fuel, etc., in the case of a diesel engine, the temperature of exhaust gas is, for example, about 250° C. to 300° C. In this case, an example of the adhesion restraining temperature is a temperature selected from the range of 300° C. to 650° C.; for example, 350° C., which is 50° C. to 100° C. higher than the temperature of exhaust gas. By heating the gas contact surface to such an adhesion restraining temperature, adhesion of particles to the gas contact surface is restrained as compared with the case where the heater section is not energized.

The effect of restraining adhesion of particles to the gas contact surface will now be described for the case where the engine is a diesel engine.

The heat generation temperature of the heater section is mostly determined by the relation between the electric power applied to the heater section and the temperature characteristic of the heat generation resistor of the heater section. Therefore, the gas contact surface can be heated to the adhesion restraining temperature (e.g., 350° C.) by applying a predetermined amount of electric power to the heater section. Since the temperature of this gas contact surface is higher than the temperature of surrounding exhaust gas (250° C. to 300° C.), in the exhaust gas around the gas contact portion surface, a temperature gradient is produced such that the temperature increases toward the gas contact surface.

Notably, a so-called thermal migration phenomenon has been known. According to this phenomenon, when a temperature gradient is present in a gas which contains floating particles, the particles within the gas move from the high temperature side toward the low temperature side in accordance with the temperature gradient.

Accordingly, when a temperature gradient as described above is produced in the gas under measurement around the gas contact surface, due to the thermal migration phenomenon, the particles within the gas under measurement are likely to move from the high temperature side toward the low temperature side in accordance with the temperature gradient; i.e., in directions away from the gas contact surface. Therefore, it is considered that, through energization of the heater section by the adhesion restraining energization means, adhesion of particles to the gas contact surface can be restrained as compared with the case where the heater section is not energized.

Further, the above-described particle detection system preferably includes burning removal energization means for heating the gas contact surface to the particle burning temperature through energization of the heater section to thereby burn and remove the adhering particles.

In this particle detection system, adhesion of particles to the gas contact surface can be restrained through the energization of the heater section by the adhesion restraining energization means. In addition, when particles has adhered to the gas contact surface (i.e., adhering particles are present), the gas contact surface can be heated to the particle burning temperature (a temperature (e.g., 700° C.) selected from the temperature range within which the adhering particles burn; for example, the temperature range of 650° C. to 700° C. or higher), whereby the adhering particles can be burned and removed. Also, the frequency at which the adhering particles are burned and removed by the burning removal energization means can be decreased as compared with the case where the system does not include the adhesion restraining energization means.

Further, any of the above-described particle detection systems is preferably configured as follows. The detection section includes an electrification section which includes an ion source for producing ions by means of gaseous discharge and which causes the produced ions to adhere to the particles floating within the gas under measurement to thereby electrify the particles so that the particles become electrified particles; the ion source has a discharge electrode member including a discharge portion at which the gaseous discharge occurs; the insulating member covers the discharge electrode member while exposing the discharge portion and has a discharge portion surrounding surface which is the gas contact surface and is located around the discharge portion; and the heater section heats the discharge portion surrounding surface of the insulating member.

When particles adhere to the discharge portion of the discharge electrode member at which gaseous discharge occurs or to a surface around the discharge portion, the state of the gaseous discharge changes, and the amount of ions which can be produced changes (for example, decreases). Therefore, the performance of detecting the particles may deteriorate; for example, the particle detection accuracy drops or the detection of the particles becomes impossible. In contrast, in the present particle detection system, the discharge portion surrounding surface of the insulating member which covers the discharge electrode member is heated by a heater. As a result, it is possible to restrain adhesion of the particles to the discharge portion surrounding surface and the discharge portion to thereby allow proper generation of gaseous discharge at the ion source, whereby the particles can be detected properly.

Any of the above-described particle detection systems is preferably as follows. The particle sensor is attached to a gas flow pipe through which the gas under measurement flows and which is maintained at a ground potential so that the detection section faces an interior of the gas flow pipe; the particle sensor includes an inner metallic member which includes a gas introduction pipe for introducing the gas under measurement into the particle sensor, which is maintained at a first potential different from the ground potential and which forms a portion of the detection section, and a tubular outer metallic member which surrounds a radially outer circumference of the inner metallic member and which is attached to the gas flow pipe to thereby be maintained at the ground potential; the insulating member is an insulating spacer which intervenes between the inner metallic member and the outer metallic member so as to electrically insulate the metallic members from each other while separating the metallic members from each other; and the heater section heats the gas contact surface of the insulating spacer.

When particles adhere to the gas contact surface of the insulating spacer intervening between the inner metallic member and the outer metallic member, the insulation between the inner metallic member maintained at the first potential and the outer metallic member maintained at the ground potential deteriorates, and a leak current flows between the first potential and the ground potential. In such a case, the detection of the signal current flowing between the first potential and the ground potential involves an error, and proper detection of the particles becomes impossible.

In contrast, in the present particle detection system, the gas contact surface of the insulating spacer is heated by the heater section. As a result, the leak current flowing between the first potential and the ground potential can be suppressed, whereby lowering of the accuracy in detecting the signal current is restrained and thus the particles can be detected properly.

BRIEF DESCRIPTION OF THE DRAWINGS

FIGS. 5A and 5B are perspective views of a first insulating spacer according to the embodiment, wherein FIG. 5A is a perspective view as viewed from a proximal end side, and FIG. 5B is a perspective view as viewed from a distal end side.

MODES FOR CARRYING OUT THE INVENTION

Figure 1:
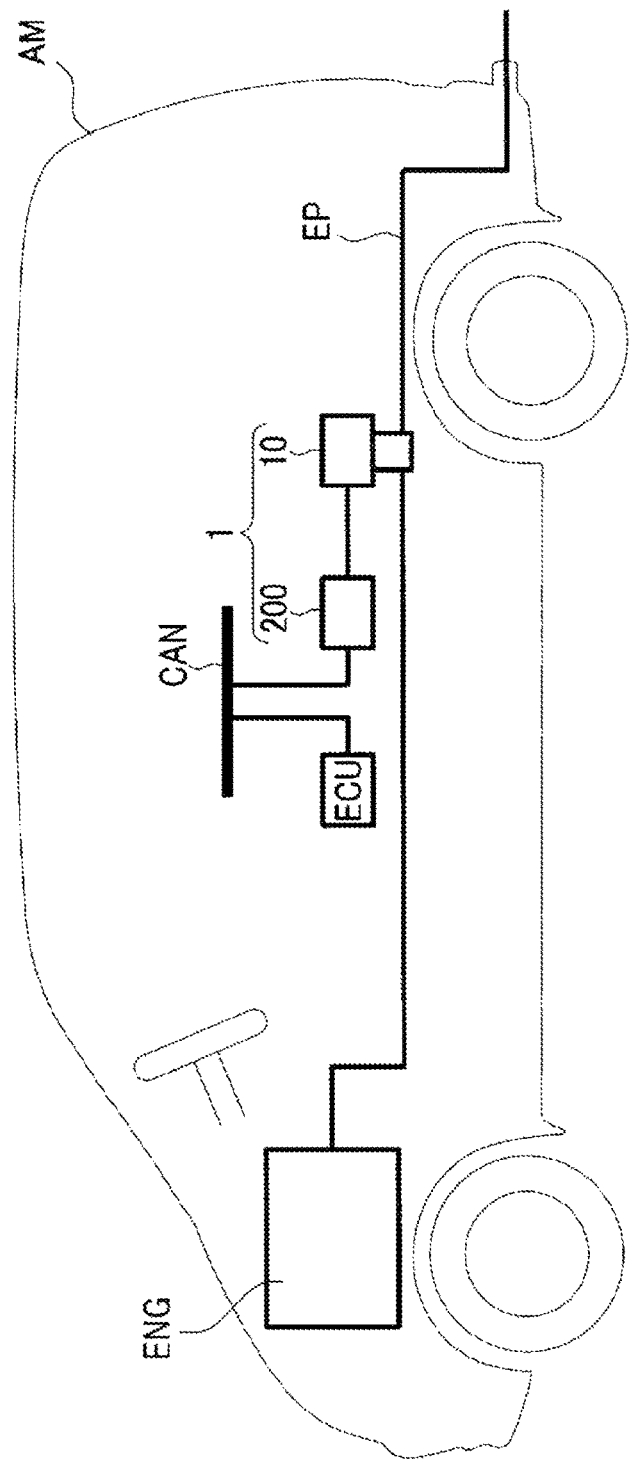
FIG. 1 is an explanatory view relating to an embodiment and describing a state in which a particle detection system is applied to an exhaust pipe of an engine mounted on a vehicle.

An embodiment of the present invention will be described with reference to the drawings. As shown in FIG. 1, a particle detection system 1 according to the present embodiment (hereinafter also referred to as the "system 1" for simplicity) is composed of a particle sensor 10 which forms a sensor main body and a circuit section 200. The particle sensor 10 is attached to an exhaust pipe EP (gas flow pipe) of an engine ENG (diesel engine in the present embodiment) mounted on a vehicle AM and detects the amount of particles S (soot, etc.) contained in exhaust gas EG (gas under measurement) flowing through the exhaust pipe EP.

This system 1 is connected, through a CAN bus, to an engine control unit ECU which controls the engine ENG.

Figure 2:
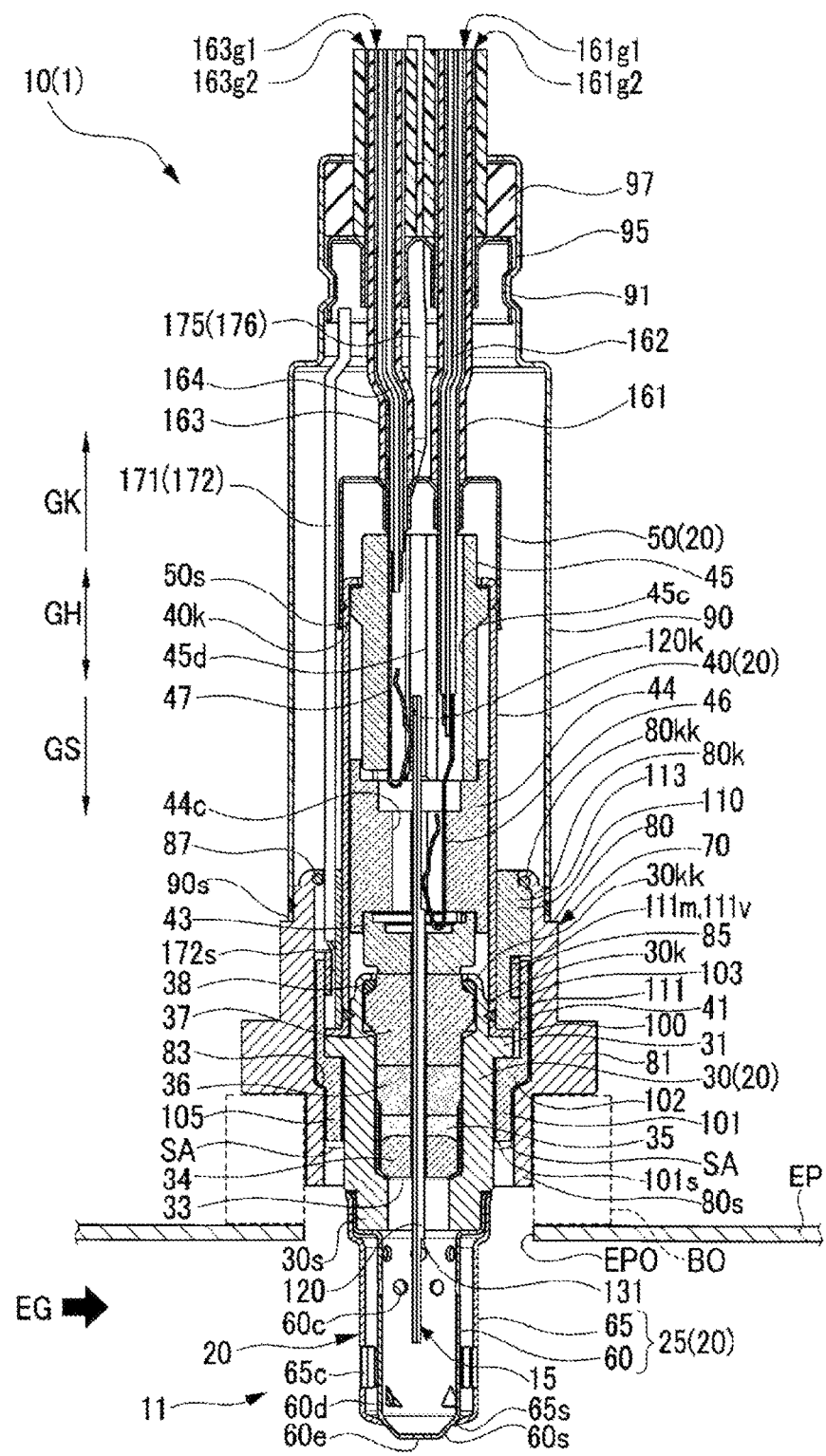
FIG. 2 is longitudinal sectional view of a particle sensor of the particle detection system according to the embodiment.
Figure 3:
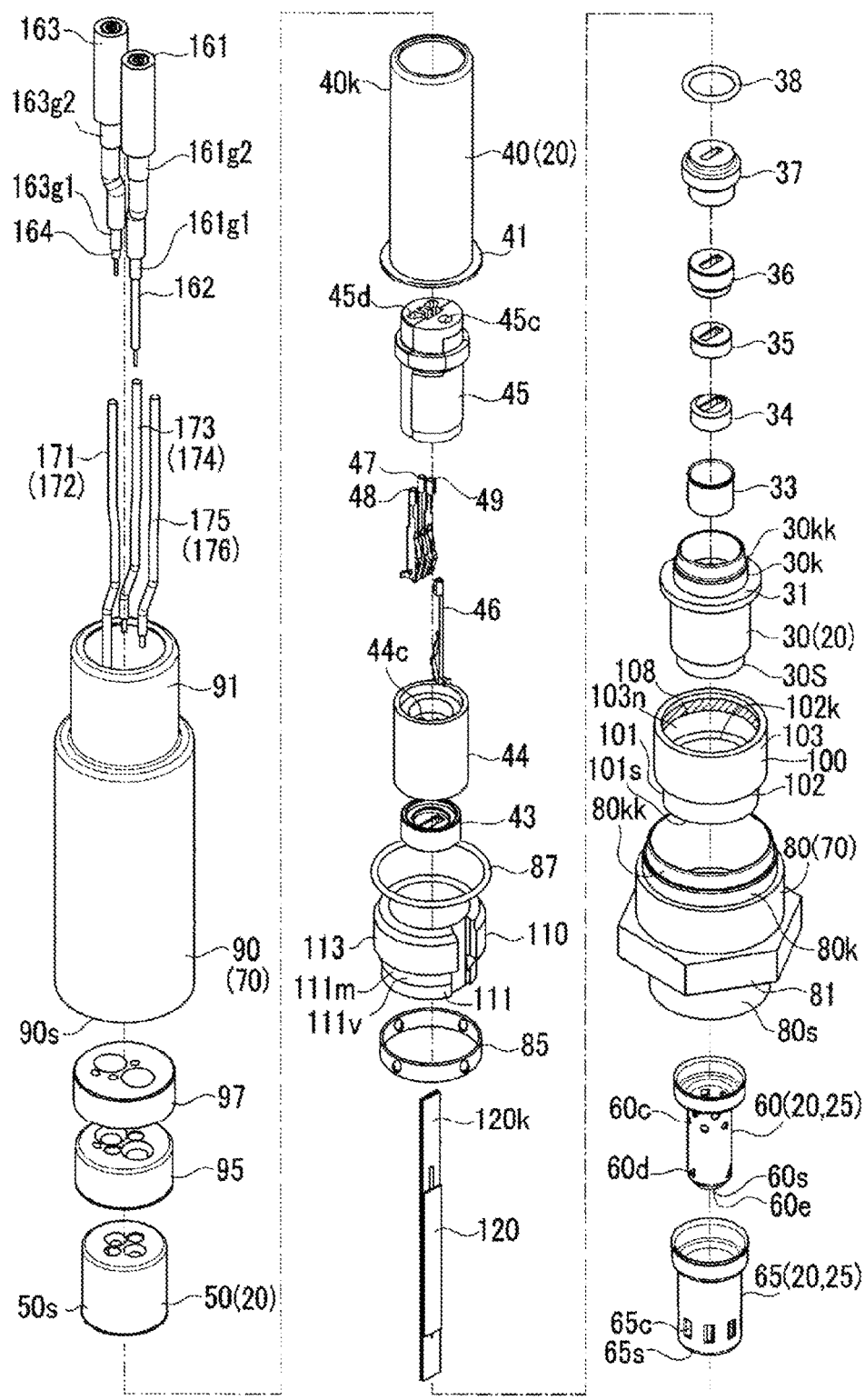
FIG. 3 is an exploded perspective view showing the structure of the particle detection sensor of the particle detection system according to the embodiment.
Figure 4:
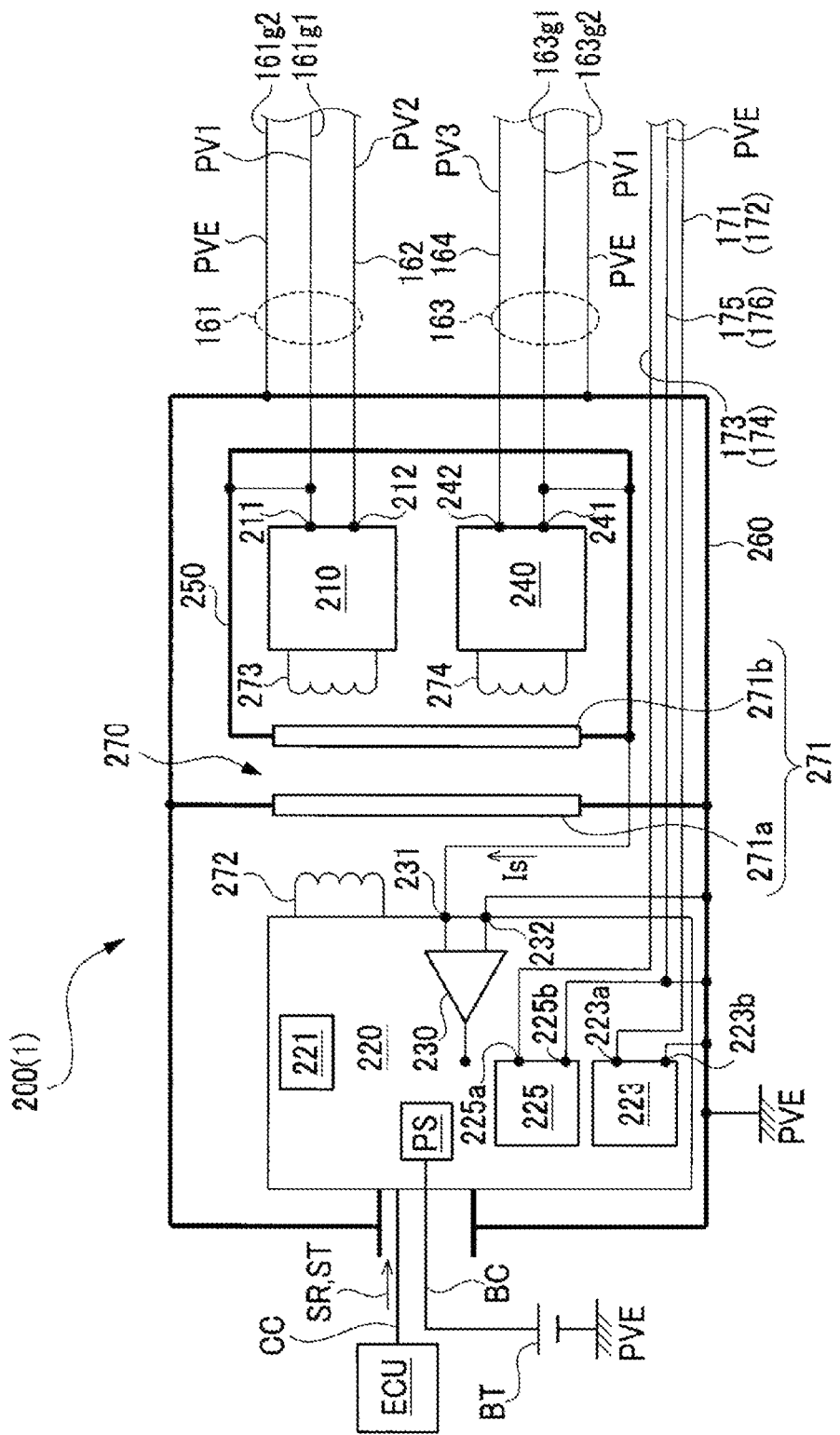
FIG. 4 is an explanatory view schematically showing the configuration of a circuit section of the particle detection system according to the embodiment.

Notably, FIGS. 2 and 3 show the structure of the particle sensor 10 of the system 1, and FIG. 4 shows the configuration of the circuit section 200 of the system 1.

First, the particle sensor 10 will be described with reference to FIGS. 2 and 3. The particle sensor 10 is composed of an inner metallic member 20 having a gas introduction pipe 25, an outer metallic member 70, a first insulating spacer 100, a second insulating spacer 110, a ceramic element 120, five electric wires 161, 163, 171, 173, 175, etc. Notably, in FIG. 2, in a longitudinal direction GH of the particle sensor 10, a side (lower side in the drawing) on which the gas introduction pipe 25 is disposed will be referred to as a distal end side GS, and a side (upper side in the drawing) which is opposite the distal end side GS and on which the electric wires 161, 163, etc., extend will be referred to as a proximal end side GK.

Notably, in the particle sensor 10, the gas introduction pipe 25 of the inner metallic member 20 and a distal end portion of the ceramic element 120 constitute a detection section 11 which is exposed to exhaust gas EG.

The particle sensor 10 is attached to the exhaust pipe EP formed of a metal and maintained at a ground potential PVE (the chassis GND of the vehicle AM) through an attachment boss BO formed of a metal (see FIG. 2). As a result, the outer metallic member 70 is maintained at the ground potential PVE. Also, the gas introduction pipe 25 which forms a distal end portion of the inner metallic member 20 is disposed within the exhaust pipe EP through a mounting opening EPO provided in the exhaust pipe EP. Ions CP are caused to adhere to the particles S contained in an introduced gas EGI introduced into the gas introduction pipe 25 through gas introduction holes 65c to thereby produce electrified particles SC, and the electrified particles SC, together with the introduced gas EGI, are discharged into the exhaust pipe EP through a gas discharge opening 60e (see FIG. 8).

The inner metallic member 20 electrically communicates with an inner circuit case 250 maintained at a first potential PV1, etc., of the circuit section 200 (to be described later) through inner-side outer conductors 161g1 and 163g1 of the electric wires 161 and 163 (to be described later) to thereby be maintained at the first potential PV1 different from the ground potential PVE. The inner metallic member 20 is composed of a metallic shell 30, an inner tube 40, an inner-tube metal connection member 50, and the gas introduction pipe 25 (an inner protector 60 and an outer protector 65).

The metallic shell 30 is a cylindrical stainless steel member extending in the longitudinal direction GH. The metallic shell 30 has an annular flange 31 projecting radially outward. A metal cup 33 is disposed within the metallic shell 30. The metal cup 33 has a hole formed in its bottom wall, and the ceramic element 120, which will be described later, extends through the hole. In the interior of the metallic shell 30, around the ceramic element 120, a cylindrical ceramic holder 34 formed of alumina, first and second powder charged layers 35 and 36 formed by compressing powder of talc, and a cylindrical ceramic sleeve 37 formed of alumina are disposed in this order from the distal end side GS toward the proximal end side GK. Notably, the ceramic holder 34 and the first powder charged layer 35 are located within the metal cup 33. Further, a crimp portion 30kk, located furthest toward the proximal end side GK, of the metallic shell 30 is crimped toward a radially inward side, thereby pressing the ceramic sleeve 37 toward the distal end side GS through a crimp ring 38.

The inner tube 40 is a cylindrical stainless steel member extending in the longitudinal direction GH. A distal end portion of the inner tube 40 is formed into an annular flange 41 projecting radially outward. The inner tube 40 is fitted onto a proximal end portion 30k of the metallic shell 30 and is laser-welded to the proximal end portion 30k with the flange 41 fitted to the flange 31.

In the interior of the inner tube 40, an insulating holder 43, a first separator 44, and a second separator 45 are disposed in this order from the distal end side GS toward the proximal end side GK. The insulating holder 43 is formed of a cylindrical insulating member and comes into contact with the ceramic sleeve 37 from the proximal end side GK. The ceramic element 120 extends through the insulating holder 43.

The first separator 44 is formed of an insulating member and has an insertion hole 44c. The insertion hole 44c allows the ceramic element 120 to extend therethrough and accommodates a distal end portion of a discharge potential terminal 46 therein. Within the insertion hole 44c, the discharge potential terminal 46 is in contact with a discharge potential pad 135 (see FIGS. 6 and 7) of the ceramic element 120.

Meanwhile, the second separator 45 is formed of an insulating member and has a first insertion hole 45c and a second insertion hole 45d. A proximal end portion of the discharge potential terminal 46 accommodated within the first insertion hole 45c, and a distal end portion of a discharge potential lead wire 162 (to be described later) are connected to each other within the first insertion hole 45c. Within the second insertion hole 45d, an element proximal-end portion 120k of the ceramic element 120 is disposed; further, an auxiliary potential terminal 47, a 2-1 heater terminal 48, and a 2-2 heater terminal 49 are accommodated in a mutually insulated condition. Also, within the second insertion hole 45d, the auxiliary potential terminal 47 is in contact with an auxiliary potential pad 147 of the ceramic element 120; the 2-1 heater terminal 48 is in contact with a 2-1 heater pad 156 of the ceramic element 120; and the 2-2 heater terminal 49 is in contact with a 2-2 heater pad 158 of the ceramic element 120 (see also FIGS. 6 and 7). Further, within the second insertion hole 45d, distal end portions of an auxiliary potential lead wire 164, a 2-1 heater lead wire 174, and a 2-2 heater lead wire 176 (to be described later) are disposed. Within the second insertion hole 45d, the auxiliary potential terminal 47 and the auxiliary potential lead wire 164 are connected to each other; the 2-1 heater terminal 48 and the 2-1 heater lead wire 174 are connected to each other; and the 2-2 heater terminal 49 and the 2-2 heater lead wire 176 are connected to each other.

The inner-tube metal connection member 50 is a stainless steel member and is fitted onto a proximal end portion 40k of the inner tube 40 while surrounding a proximal end portion of the second separator 45, and a distal end portion 50s of the inner-tube metal connection member 50 is laser-welded to the proximal end portion 40k of the inner tube 40. The four electric wires 161, 163, 173, and 175 are passed through the inner-tube metal connection member 50. The electric wire 171 is not passed through the inner-tube metal connection member 50. Of these electric wires, the inner-side outer conductors 161g1 and 163g1 of the electric wires 161 and 163, which are triple coaxial cables as will be described later, are connected to the inner-tube metal connection member 50.

The gas introduction pipe 25 is composed of the inner protector 60 and the outer protector 65. The inner protector 60 is a closed-bottomed cylindrical member formed of stainless steel, and the outer protector 65 is a cylindrical member formed of stainless steel. The outer protector 65 is disposed around the inner protector 60 with respect to the radial direction. The inner protector 60 and the outer protector 65 are fitted onto a distal end portion 30s of the metallic shell 30 and are laser-welded to the distal end portion 30s. The gas introduction pipe 25 surrounds, from the radially outward side, a distal end portion (an ion source 15 to be described later) of the ceramic element 120 projecting from the metallic shell 30 toward the distal end side GS to thereby protect the ceramic element 120 from water droplets and foreign substances as well as introduce the exhaust gas EG to a space around the ceramic element 120.

The outer protector 65 has a plurality of the rectangular gas introduction holes 65c formed in a distal end portion thereof for introducing the exhaust gas EG into the interior thereof. Also, the inner protector 60 has a plurality of circular first inner introduction holes 60c formed in a proximal end portion thereof for introducing, into the interior thereof, the introduced gas EGI introduced into the outer protector 65. The inner protector 60 also has a plurality of triangular second inner introduction holes 60d formed in a distal end portion thereof. Further, the inner protector 60 has the circular gas discharge opening 60e formed in a bottom wall thereof for discharging the introduced gas EGI into the exhaust pipe EP, and its distal end portion 60s, including the gas discharge opening 60e, projects toward the distal end side GS from a distal end opening 65s of the outer protector 65.

Figure 8:
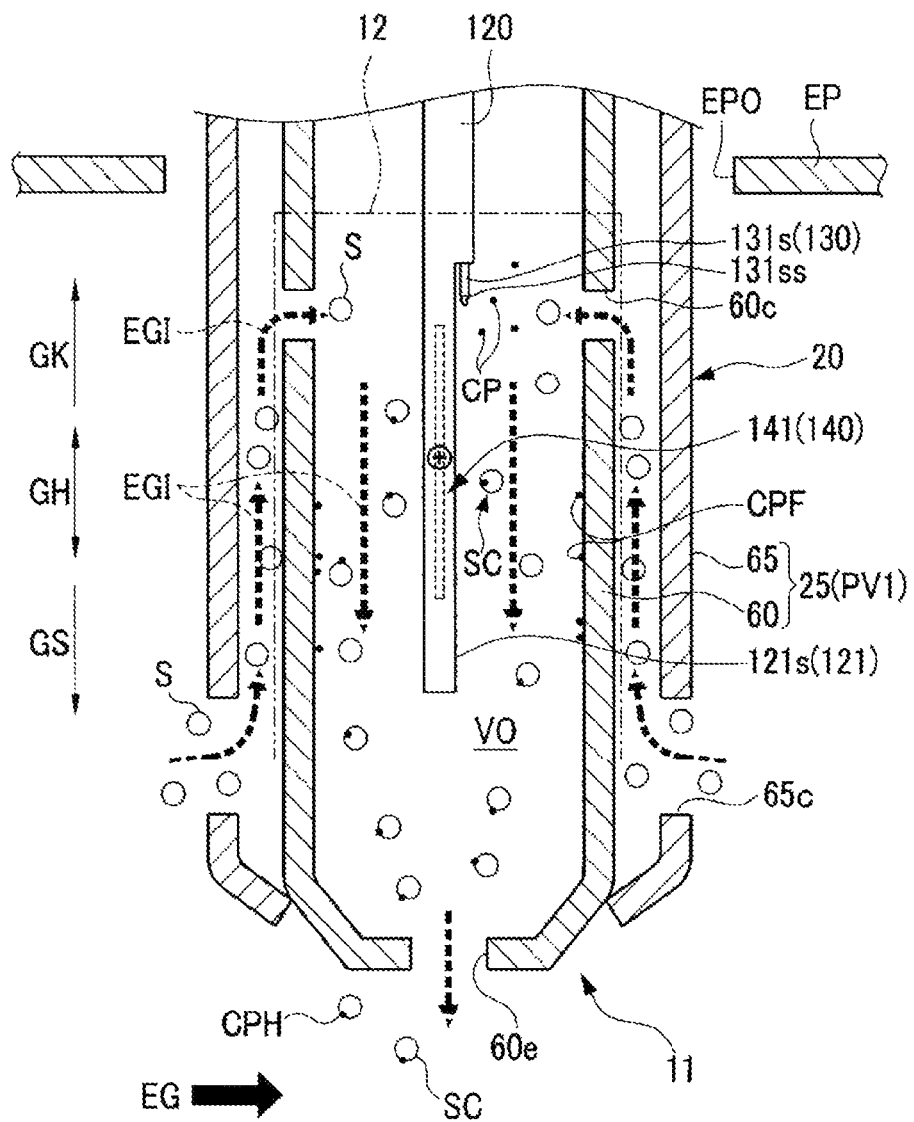
FIG. 8 is an explanatory view schematically showing the electrical function and operation of the particle detection system according to the embodiment, and introduction and discharge of exhaust gas.

Here, there will be described the introduction and discharge of the exhaust gas EG into and from the interiors of the inner protector 60 and the outer protector 65 when the particle sensor 10 is used (see FIG. 8). In FIG. 8, the exhaust gas EG flows within the exhaust pipe EP from the left-hand side toward the right-hand side. When the exhaust gas EG passes through a region around the outer protector 65 and the inner protector 60, its flow velocity increases on the outer side of the gas discharge opening 60e of the inner protector 60, and a negative pressure is produced near the gas discharge opening 60e due to the so-called Venturi effect.

By this negative pressure, the introduced gas EGI introduced into the inner protector 60 is discharged to the exhaust pipe EP through the gas discharge opening 60e. Simultaneously, the exhaust gas EG around the gas introduction holes 65c of the outer protector 65 is introduced into the interior of the outer protector 65 through the gas introduction holes 65c, and is further introduced into the interior of the inner protector 60 through the first inner introduction holes 60c of the inner protector 60. The introduced gas EGI within the inner protector 60 is discharged through the gas discharge opening 60e. Thus, as indicated by the broken line arrow, a flow of the introduced gas EGI from the first inner introduction holes 60c on the proximal end side GK toward the gas discharge opening 60e on the distal end side GS is produced within the inner protector 60.

Next, the outer metallic member 70 will be described. The outer metallic member 70 is formed of a cylindrical metal material, surrounds the radially outer circumference of the inner metallic member 20 while being separated from the inner metallic member 20, and is attached to the exhaust pipe EP maintained at the ground potential PVE (the chassis GND of the vehicle AM), whereby the outer metallic member 70 is maintained at the ground potential PVE. The outer metallic member 70 is composed of a mounting metallic member 80 and an outer tube 90.

The mounting metallic member 80 is a cylindrical stainless steel member extending in the longitudinal direction GH. The mounting metallic member 80 is disposed to radially surround the metallic shell 30 of the inner metallic member 20 and a distal end portion of the inner tube 40 of the inner metallic member 20 in such a manner as to be separated from them. The mounting metallic member 80 has a flange portion 81 which projects toward the radially outward side so as to form a hexagonal outer shape. The mounting metallic member 80 has an internal stepped portion 83. The mounting metallic member 80 also has a male screw (not shown) used for fixation to the exhaust pipe EP and formed on the outer circumference of its distal end portion 80s located on the distal end side GS of the flange portion 81. By means of the male screw of the distal end portion 80s, the particle sensor 10 is attached to an attachment boss BO which is formed of metal and is separately fixed to the exhaust pipe EP, whereby the particle sensor 10 is fixed to the exhaust pipe EP via the attachment boss BO.

The first insulating spacer 100 and the second insulating spacer 110 (to be described later) are disposed between the mounting metallic member 80 and the inner metallic member 20. Further, a heater metal connection member 85 (to be described later) and a distal end portion 172s of a 1-1 heater lead wire 172 of the electric wire 171 connected to the heater metal connection member 85 are disposed between the mounting metallic member 80 and the inner metallic member 20. A crimp portion 80kk, located furthest toward the proximal end side GK, of the mounting metallic member 80 is crimped toward the radially inward side, thereby pressing the second insulating spacer 110 toward the distal end side GS through a line packing 87.

The outer tube 90 is a tubular stainless steel member extending in the longitudinal direction GH. A distal end portion 90s of the outer tube 90 is fitted onto a proximal end portion 80k of the mounting metallic member 80 and is laser-welded to the proximal end portion 80k. An outer-tube metal connection member 95 is disposed in the interior of a small diameter portion 91 of the outer tube 90 located on the proximal end side GK; further, a grommet 97 formed of fluororubber is disposed on the proximal end side GK of the outer-tube metal connection member 95 in the interior of the small diameter portion 91. The five electric wires 161, 163, 171, 173, and 175 (to be described later) are passed through the outer-tube metal connection member 95 and the grommet 97. Of these electric wires, outer-side outer conductors 161g2 and 163g2 of the electric wires 161 and 163, which are triple coaxial cables as will be described later, are connected to the outer-tube metal connection member 95. The outer-tube metal connection member 95 is crimped together with the small diameter portion 91 of the outer tube 90 so that the diameter of the outer-tube metal connection member 95 decreases toward the radially inward side; thus, the outer-tube metal connection member 95 and the grommet 97 are fixed within the small diameter portion 91 of the outer tube 90.

Figure 5A:
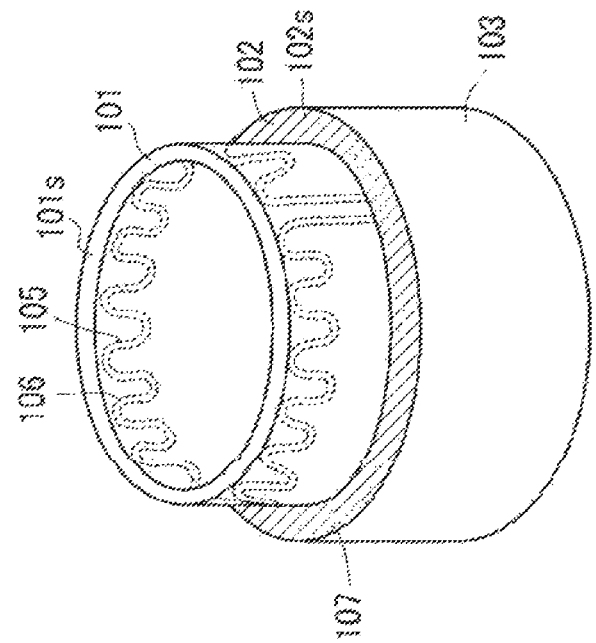
Figure 5B:
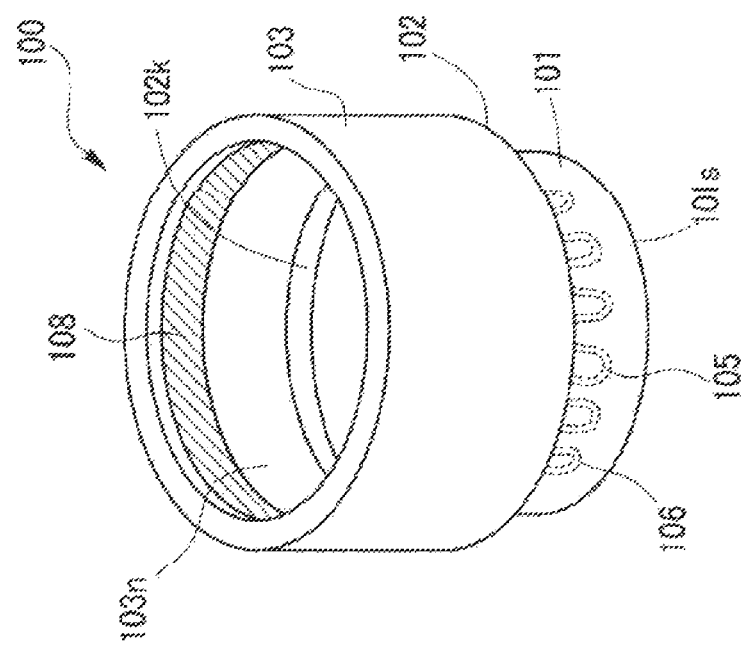

Next, the first insulating spacer 100 will be described (see also FIG 5A and FIG 5B). The first insulating spacer 100 is a cylindrical insulating member formed of alumina which is an insulating material and extending in the longitudinal direction GH. The first insulating spacer 100 is interposed between the inner metallic member 20 and the outer metallic member 70 so as to electrically insulate them from each other while separating them from each other. Specifically, the first insulating spacer 100 is disposed between the mounting metallic member 80 of the outer metallic member 70 and the metallic shell 30 and a distal end portion of the inner tube 40 of the inner metallic member 20. The first insulating spacer 100 is composed of a spacer distal end portion 101 having a small diameter and located on the distal end side GS, a spacer proximal end portion 103 having a large diameter and located on the proximal end side GK, and a spacer intermediate portion 102 which connects the spacer distal end portion 101 and the spacer proximal end portion 103.

In a state in which the particle sensor 10 is attached to the exhaust pipe EP, a distal end portion of the spacer distal end portion 101 is exposed to the interior of the exhaust pipe EP (faces the interior of the exhaust pipe EP) so as to serve as a gas contact portion 101s which comes into contact with the exhaust gas EG flowing through the exhaust pipe EP.

The spacer intermediate portion 102 has an outer shoulder surface 102s which faces the distal end side GS, and an inner shoulder surface 102k which faces the proximal end side GK. The outer shoulder surface 102s and the inner shoulder surface 102k are annular surfaces extending in the circumferential direction of the first insulating spacer 100. The outer shoulder surface 102s comes into contact with the stepped portion 83 of the mounting metallic member 80 from the proximal end side GK over the entire circumference thereof. Meanwhile, the flange 31 of the metallic shell 30 comes into contact with the inner shoulder surface 102k from the proximal end side GK.

The first insulating spacer 100 has a spacer heater 105 embedded therein and adapted to heat the gas contact portion 101s. Specifically, the spacer heater 105 has a heat generation resistor 106 formed of tungsten, and paired 1-1 heater terminal 107 and 1-2 heater terminal 108 electrically communicating with opposite ends of the heat generation resistor 106. The heat generation resistor 106 is embedded in the spacer distal end portion 101 in a meandering manner over the entire circumference thereof. The 1-1 heater terminal 107 is formed on the outer shoulder surface 102s of the spacer intermediate portion 102 and electrically communicates with the mounting metallic member 80. Specifically, the 1-1 heater terminal 107 is formed on the entire surface of the outer shoulder surface 102s to have an annular shape extending in the circumferential direction of the first insulating spacer 100 to thereby come into contact with the stepped portion 83 of the mounting metallic member 80 over the entire circumference thereof.

Meanwhile, the 1-2 heater terminal 108 is formed on a proximal end portion of an inner circumferential surface 103n of the spacer proximal end portion 103 to have a cylindrical shape extending in the circumferential direction of the first insulating spacer 100. The cylindrical heater metal connection member 85 is disposed on the radially inward side of the spacer proximal end portion 103 and is in contact with the 1-2 heater terminal 108 formed on the inner circumferential surface 103n of the spacer proximal end portion 103. The distal end portion 172s of the 1-1 heater lead wire 172 of the electric wire 171 (to be described later) is connected to the heater metal connection member 85. The electric wire 171 extends in a region between the inner metallic member 20 and the outer metallic member 70 from the heater metal connection member 85 toward the proximal end side GK and extends to the outer side of the outer metallic member 70.

Next, the second insulating spacer 110 will be described. The second insulating spacer 110 is a tubular member formed of alumina and extending in the longitudinal direction GH. The second insulating spacer 110 is interposed between the inner metallic member 20 and the outer metallic member 70 so as to electrically insulate them from each other while separating from each other. Specifically, the second insulating spacer 110 is disposed between a distal end portion of the inner tube 40 of the inner metallic member 20 and the mounting metallic member 80 of the outer metallic member 70. The second insulating spacer 110 is composed of a distal end portion 111 located on the distal end side GS and a proximal end portion 113 located on the proximal end side GK.

The distal end portion 111 is smaller in outside diameter and thickness than the proximal end portion 113. The distal end portion 111 is disposed between the inner tube 40 and the spacer proximal end portion 103 of the first insulating spacer 100. A groove 111v extending in the circumferential direction of the second insulating spacer 110 is formed on an outer circumferential surface 111m of the distal end portion 111 over the entire circumference thereof, and the aforementioned heater metal connection member 85 is disposed in the groove 111v. Meanwhile, the proximal end portion 113 is located on the proximal end side GK of the spacer proximal end portion 103 of the first insulating spacer 100 and is disposed between the mounting metallic member 80 and the inner tube 40.

As mentioned above, the crimp portion 80kk of the mounting metallic member 80 presses the second insulating spacer 110 toward the forward end side GS through the line packing 87. Thus, the distal end portion 111 of the second insulating spacer 110 presses the flange 41 of the inner tube 40 and the flange 31 of the metallic shell 30 toward the distal end side GS. Further, these flanges 41 and 31 press the spacer intermediate portion 102 of the first insulating spacer 100 toward the distal end side GS, whereby the spacer intermediate portion 102 is engaged with the stepped portion 83 of the mounting metallic member 80. Thus, the first insulating spacer 100 and the second insulating spacer 110 are fixed between the inner metallic member 20 (the metallic shell 30 and a distal end portion of the inner tube 40) and the outer metallic member 70 (mounting metallic member 80).

Figure 6:
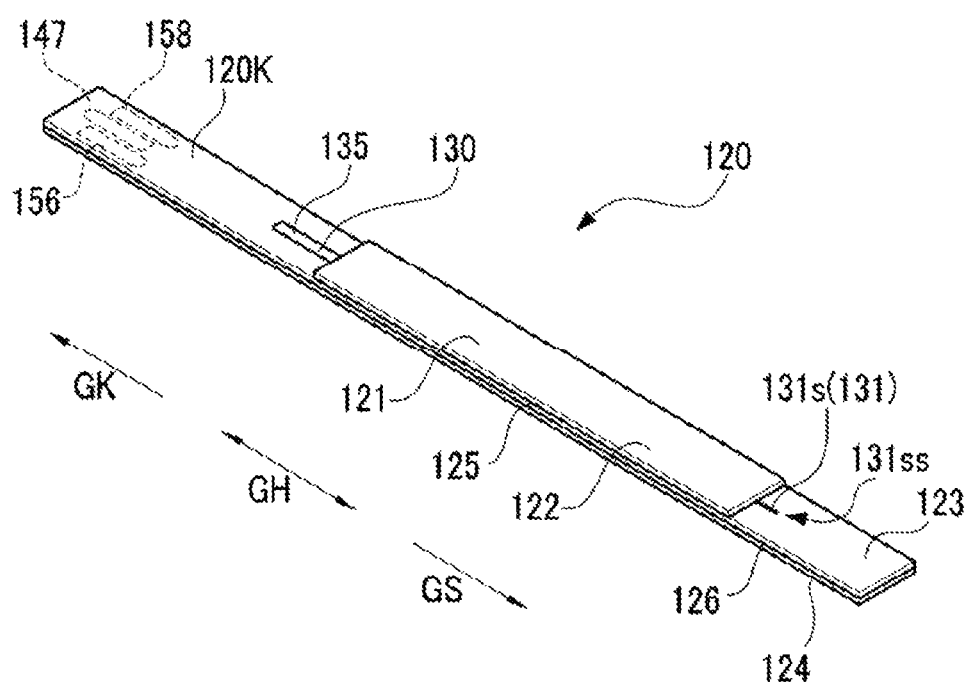
FIG. 6 is a perspective view of a ceramic element according to the embodiment.
Figure 7:
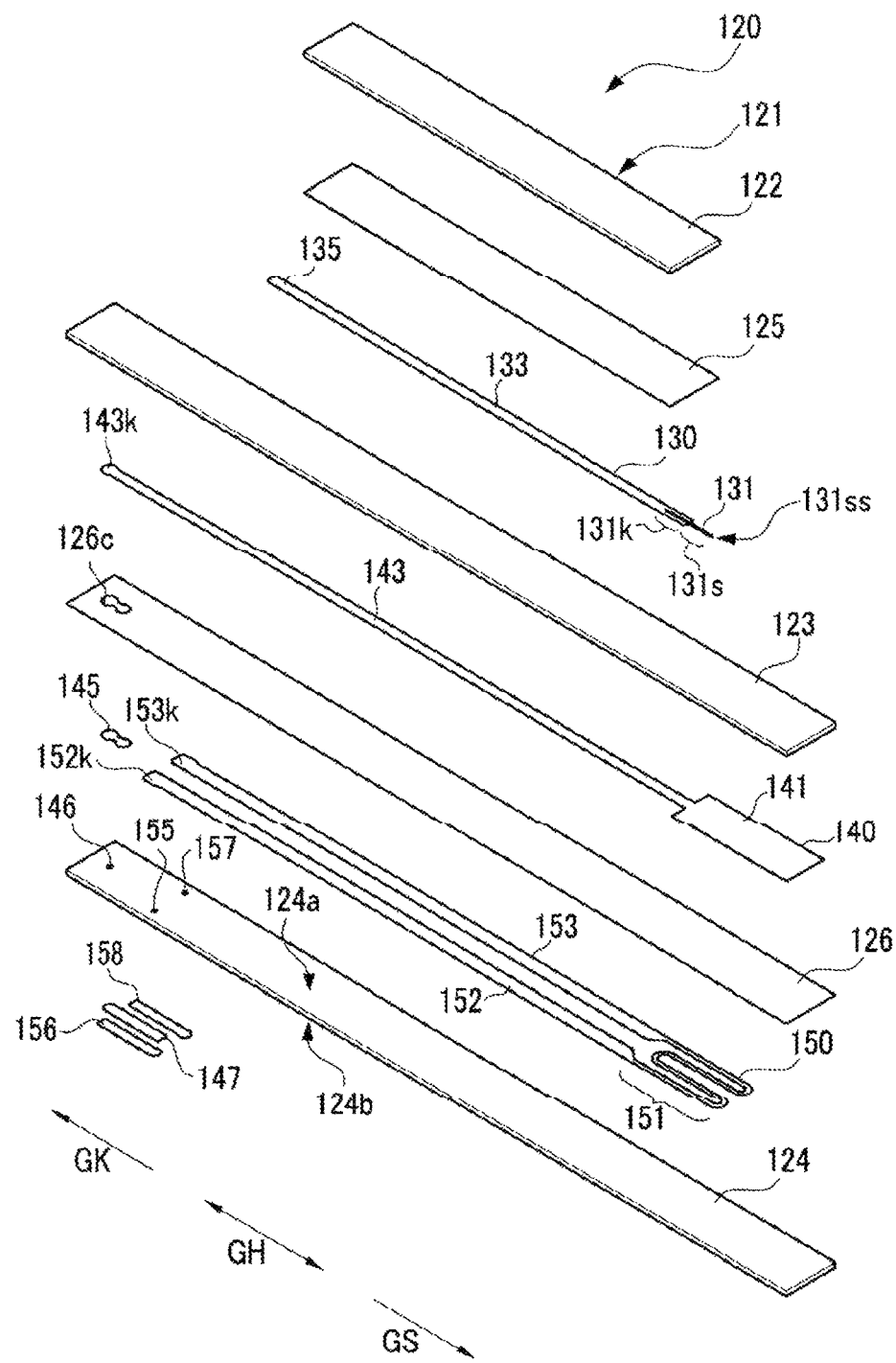
FIG. 7 is an exploded perspective view of the ceramic element according to the embodiment.

Next, the ceramic element 120 will be described (see also FIGS. 6 and 7). The ceramic element 120 has a plate-shaped ceramic substrate 121 (insulating member) formed of alumina which is an insulating material and extending in the longitudinal direction GH. A discharge electrode member 130, an auxiliary electrode member 140, and an element heater 150 are embedded in the ceramic substrate 121, and are integrated through firing (integral firing). Specifically, the ceramic substrate 121 is a ceramic laminate in which three ceramic layers 122, 123, and 124 formed of alumina originating from an alumina green sheet are layered together, and two insulating cover layers 125 and 126 of alumina are formed between these layers by means of printing. The ceramic layer 122 and the insulating cover layer 125 are shorter than the ceramic layers 123 and 124 and the insulating cover layer 126 as measured on the distal end side GS and the proximal end side GK in the longitudinal direction GH. The discharge electrode member 130 is disposed between the insulating cover layer 125 and the ceramic layer 123. Also, the auxiliary electrode member 140 is disposed between the ceramic layer 123 and the insulating cover layer 126, and the element heater 150 is disposed between the insulating cover layer 126 and the ceramic layer 124.

The discharge electrode member 130 extends in the longitudinal direction GH and is composed of a needle-shaped electrode portion 131 located at the distal end side GS, a discharge potential pad 135 located at the proximal end side GK, and a lead portion 133 extending therebetween. The needle-shaped electrode portion 131 is formed of a platinum wire. Meanwhile, the lead portion 133 and the discharge potential pad 135 are formed of tungsten by means of pattern printing. A proximal end portion 131k of the needle-shaped electrode portion 131 and the lead portion 133 of the discharge electrode member 130 are entirely embedded in the ceramic substrate 121. Meanwhile, a distal end portion 131s of the needle-shaped electrode portion 131 projects from the ceramic substrate 121 on the distal end side GS of the ceramic layer 122 of the ceramic substrate 121. As a result, the distal end portion of the ceramic element 120, including the distal end portion 131s of the needle-shaped electrode portion 131, constitutes the ion source 15 which produces ions CP by means of corona discharge (which will be described later). In the ion source 15, a needle-shaped end portion 131ss of the distal end portion 131s of the needle-shaped electrode portion 131 serves as a discharge portion at which corona discharge (gaseous discharge) occurs. As will be described later, corona discharge (gaseous discharge) occurs between the needle-shaped end portion 131ss and the inner protector 60, whereby the ions CP are produced.

Notably, the surface of a distal end portion of the ceramic substrate 121 is a gas contact surface 121s which comes into contact with the exhaust gas EG introduced into the gas introduction pipe 25 (the inner protector 60 and the outer protector 65) (see FIG. 8).

Also, the discharge potential pad 135 is exposed on the proximal end side GK of the ceramic layer 122 of the ceramic substrate 121. As mentioned above, the discharge potential terminal 46 is in contact with the discharge potential pad 135 within the insertion hole 44c of the first separator 44.

The auxiliary electrode member 140 extends in the longitudinal direction GH, is formed by means of pattern printing, and is entirely embedded in the ceramic substrate 121. The auxiliary electrode member 140 is composed of a rectangular auxiliary electrode portion 141 located at the distal end side GS and a lead portion 143 connected to the auxiliary electrode portion 141 and extending toward the proximal end side GK. A proximal end portion 143k of the lead portion 143 is connected to a conductor pattern 145 formed on one main surface 124a of the ceramic layer 124 through a through hole 126c of the insulating cover layer 126. Further, the conductor pattern 145 is connected to the auxiliary potential pad 147 formed on the other main surface 124b of the ceramic layer 124 via a through hole conductor 146 formed in the ceramic layer 124 in such a manner as to extend therethrough. As mentioned above, the auxiliary potential terminal 47 is in contact with the auxiliary potential pad 147 within the second insertion hole 45d of the second separator 45.

The element heater 150 is formed by means of pattern printing and is entirely embedded in the ceramic substrate 121. The element heater 150 is composed of a heat generation resistor 151 located at the distal end side GS for heating the ceramic element 120, and paired heater lead portions 152 and 153 connected to the opposite ends of the heat generation resistor 151 and extending toward the proximal end side GK. A proximal end portion 152k of one heater lead portion 152 is connected to the 2-1 heater pad 156 formed on the other main surface 124b of the ceramic layer 124 via a through hole conductor 155 formed in the ceramic layer 124 in such a manner as to extend therethrough. As mentioned above, the 2-1 heater terminal 48 is in contact with the 2-1 heater pad 156 within the second insertion hole 45d of the second separator 45. Also, a proximal end portion 153k of the other heater lead portion 153 is in contact with the 2-2 heater pad 158 formed on the other main surface 124b of the ceramic layer 124 via a through hole conductor 157 formed in the ceramic layer 124 in such a manner as to extend therethrough. As mentioned above, the 2-2 heater terminal 49 is in contact with the 2-2 heater pad 158 within the second insertion hole 45*d* of the second separator 45.

Next, the electric wires 161, 163, 171, 173, and 175 will be described. Of these five electric wires, the two electric wires 161 and 163 are triple coaxial cables (triaxial cables), and the remaining three electric wires 171, 173, and 175 are small-diameter single-core insulated electric wires.

Of these electric wires, the electric wire 161 has the discharge potential lead wire 162 as a core wire (center conductor). As mentioned above, the discharge potential lead wire 162 is connected to the discharge potential terminal 46 within the first insertion hole 45*c* of the second separator 45. Also, the electric wire 163 has the auxiliary potential lead wire 164 as a core wire (center conductor). The auxiliary potential lead wire 164 is connected to the auxiliary potential terminal 47 within the second insertion hole 45*d* of the second separator 45. Of the coaxial double outer conductors of the electric wires 161 and 163, the inner-side outer conductors 161*g*1 and 163*g*1 located on the inner side are connected to the inner-tube metal connection member 50 of the inner metallic member 20 to thereby be maintained at the first potential PV1. Meanwhile, the outer-side outer conductors 161*g*2 and 163*g*2 located on the outer side are connected to the outer-tube metal connection member 95 electrically communicating with the outer metallic member 70 to thereby be maintained at the ground potential PVE.

Also, the electric wire 171 has the 1-1 heater lead wire 172 as a core wire. The 1-1 heater lead wire 172 is, as mentioned above, connected to the heater metal connection member 85 in the interior of the mounting metallic member 80. The electric wire 173 has the 2-1 heater lead wire 174 as a core wire. The 2-1 heater lead wire 174 is connected to the 2-1 heater terminal 48 within the second insertion hole 45*d* of the second separator 45. The electric wire 175 has the 2-2 heater lead wire 176 as a core wire. The 2-2 heater lead wire 176 is connected to the 2-2 heater terminal 49 within the second insertion hole 45*d* of the second separator 45.

Next, the circuit section 200 will be described (see FIG. 4). The circuit section 200 has a circuit which is connected to the electric wires 161, 163, 171, 173, and 175 of the particle sensor 10 and which drives the particle sensor 10 and detects a signal current Is (to be described later). The circuit section 200 has an ion source power supply circuit 210, an auxiliary electrode power supply circuit 240, and a measurement control circuit 220.

The ion source power circuit 210 has a first output terminal 211 maintained at the first potential PV1 and a second output terminal 212 maintained at a second potential PV2. The second potential PV2 is a positive high potential in relation to the first potential PV1.

The auxiliary electrode power supply circuit 240 has an auxiliary first output terminal 241 maintained at the first potential PV1 and an auxiliary second output terminal 242 maintained at an auxiliary electrode potential PV3. The auxiliary electrode potential PV3 is a positive high DC potential in relation to the first potential PV1, but is lower than a peak potential of the second potential PV2.

The measurement control circuit 220 has a signal current detection circuit 230, a first heater energization circuit 223, and a second heater energization circuit 225. The signal current detection circuit 230 has a signal input terminal 231 maintained at the first potential PV1 and a ground input terminal 232 maintained at the ground potential PVE. The ground potential PVE and the first potential PV1 are insulated from each other, and the signal current detection circuit 230 detects the signal current Is flowing between the signal input terminal 231 (first potential PV1) and the ground input terminal 232 (ground potential PVE).

The first heater energization circuit 223 energizes the spacer heater 105 of the first insulating spacer 100 by PWM control for heating the spacer heater 105 and has a 1-1 heater energization terminal 223*a* connected to the 1-1 heater lead wire 172 of the electric wire 171 and a 1-2 heater energization terminal 223*b* maintained at the ground potential PVE.

Notably, the 1-1 heater terminal 107 of the spacer heater 105 electrically communicates with the 1-1 heater energization terminal 223*a* of the first heater energization circuit 223 through the heater connection metallic member 85 and the 1-1 heater lead wire 172 of the electric wire 171. Also, the 1-2 heater terminal 108 of the spacer heater 105 electrically communicates with the 1-2 heater energization terminal 223*b* of the first heater energization circuit 223, which is maintained at the ground potential PVE, through the outer metallic member 70 and the outer-tube metal connection member 95.

Therefore, when a predetermined heater energization voltage from the first heater energization circuit 223 is applied between the 1-1 heater terminal 107 and the 1-2 heater terminal 108 of the spacer heater 105, the heat generation resistor 106 of the spacer heater 105 generates heat upon energization. As a result, the spacer distal end portion 101 of the first insulating spacer 100 is heated, whereby adhering particles SA (see FIG. 2); i.e., soot (particles S) adhering to the gas contact portion 101*s* of the spacer distal end portion 101, are burned and removed.

The second heater energization circuit 225 energizes the element heater 150 of the ceramic element 120 by PWM control so as to cause the element heater 150 to generate heat and has a 2-1 heater energization terminal 225*a* connected to the 2-1 heater lead wire 174 of the electric wire 173 and a 2-2 heater energization terminal 225*b* connected to the 2-2 heater lead wire 176 of the electric wire 175 and maintained at the ground potential PVE.

Notably, the 2-1 heater pad 156 of the element heater 150 electrically communicates with the 2-1 heater energization terminal 225*a* of the second heater energization circuit 225 through the 2-1 heater terminal 48 and the 2-1 heater lead wire 174 of the electric wire 173. Also, the 2-2 heater pad 158 of the element heater 150 electrically communicates with the 2-2 heater energization terminal 225*b* of the second heater energization circuit 225 through the 2-2 heater terminal 49 and the 2-2 heater lead wire 176 of the electric wire 175.

Figure 9:
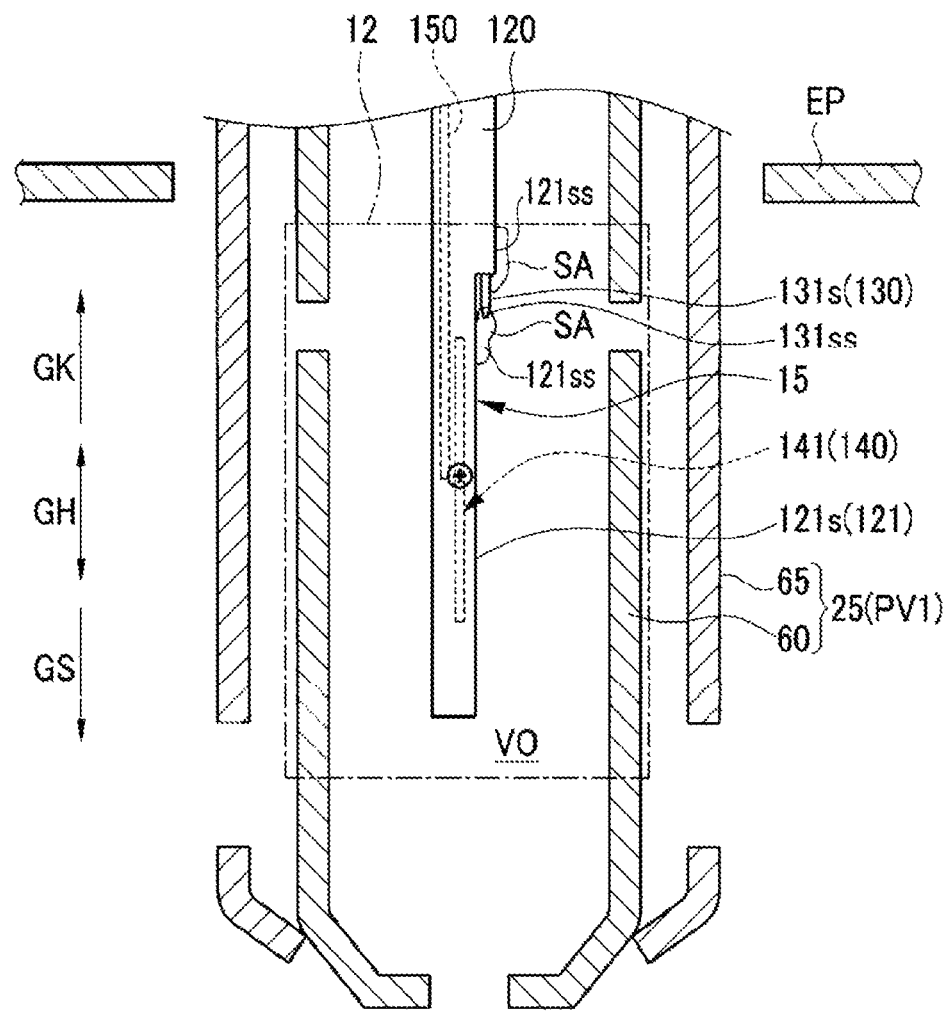
FIG. 9 is an explanatory view showing particles adhering to a gas contact portion of the ceramic element of the particle detection system according to the embodiment and an element heater heating them.

Therefore, when a predetermined heater energization voltage from the second heater energization circuit 225 is applied between the 2-1 heater pad 156 and the 2-2 heater pad 158 of the element heater 150, the heat generation resistor 151 of the element heater 150 generates heat upon energization. As a result, the ceramic element 120 (a discharge portion surrounding surface 121*ss* of the gas contact surface 121*s* of the ceramic substrate 121 located around the needle-shaped end portion 131*ss* (discharge portion) of the needle-shaped electrode portion 131) is heated, whereby adhering particles SA (see FIG. 9); i.e., soot (particles S) adhering to the ceramic element 120 (the discharge portion surrounding surface 121*ss* of the ceramic substrate 121 and the needle-shaped end portion 131*ss* of the needle-shaped electrode portion 131), are burned and removed.

In the circuit section 200, the ion source power supply circuit 210 and the auxiliary electrode power supply circuit 240 are surrounded by an inner circuit case 250 maintained at the first potential PV1. Also, the inner circuit case 250 accommodates and surrounds a secondary iron core 271b of an insulated transformer 270 and electrically communicates with the inner-side outer conductors 161g1 and 163g1 maintained at the first potential PV1 of the electric wires 161 and 163. The insulated transformer 270 is configured such that its iron core 271 is divided into a primary iron core 271a having a primary coil 272 wound thereon and the secondary iron core 271b having a power-supply-circuit-side coil 273 and an auxiliary-electrode-power-supply-side coil 274 wound thereon. The primary iron core 271a electrically communicates with the ground potential PVE, and the secondary iron core 271b electrically communicates with the first potential PV1.

Further, the ion source power supply circuit 210, the auxiliary electrode power supply circuit 240, the inner circuit case 250, and the measurement control circuit 220 are surrounded by an outer circuit case 260 maintained at the ground potential PVE. Also, the outer circuit case 260 accommodates and surrounds the primary iron core 271a of the insulated transformer 270 and electrically communicates with the outer-side outer conductors 161g2 and 163g2 maintained at the ground potential PVE of the electric wires 161 and 163.

The measurement control circuit 220 has a built-in regulator power supply PS. The regulator power supply PS is driven by an external battery BT through a power supply wiring BC. A portion of electric power input to the measurement control circuit 220 through the regulator power supply PS is distributed to the ion source power supply circuit 210 and the auxiliary electrode power supply circuit 240 via the insulated transformer 270. The measurement control circuit 220 also has a microprocessor 221 and can communicate, through a communication line CC (specifically, through the CAN bus as shown in FIG. 1), with an engine control unit ECU (hereinafter also referred to as the "ECU" for simplicity). Thus, the measurement control circuit 220 can send signals indicative of results of measurement (the magnitude of the signal current Is) by the aforementioned signal current detection circuit 230, etc., to the ECU.

Next, the electrical function and operation of the particle detection system 1 will be described (see FIGS. 8 and 4). The discharge electrode member 130 of the ceramic element 120 is connected to and electrically communicates with the second output terminal 212 of the ion source power supply circuit 210 through the discharge potential lead wire 162 of the electric wire 161 to thereby be maintained at the second potential PV2. Meanwhile, the auxiliary electrode member 140 of the ceramic element 120 is connected to and electrically communicates with the auxiliary second output terminal 242 of the auxiliary electrode power supply circuit 240 through the auxiliary potential lead wire 164 of the electric wire 163 to thereby be maintained at the auxiliary electrode potential PV3. Further, the inner metallic member 20 is connected to and electrically communicates with the inner circuit case 250, etc., through the inner-side outer conductors 161g1 and 163g1 of the electric wires 161 and 163 to thereby be maintained at the first potential PV1. Additionally, the outer metallic member 70 is connected to and electrically communicates with the outer circuit case 260, etc., through the outer-side outer conductors 161g2 and 163g2 of the electric wires 161 and 163 to thereby be maintained at the ground potential PVE.

The second potential PV2 of a positive high voltage (e.g., 1 kV to 2 kV) is applied from the ion source power supply circuit 210 of the circuit section 200 to the needle-shaped electrode portion 131 of the discharge electrode member 130 through the discharge potential lead wire 162 of the electric wire 161, the discharge potential terminal 46, and the discharge potential pad 135. As a result, gaseous discharge; specifically, corona discharge, occurs between the needle-shaped end portion 131ss of the needle-shaped electrode portion 131 and the inner protector 60 maintained at the first potential PV1, whereby ions CP are generated around the needle-shaped end portion 131ss. As described above, by the action of the gas introduction pipe 25, the exhaust gas EG is introduced into the interior of the inner protector 60, and a flow of the introduced gas EGI from the proximal end side GK toward the distal end side GS is produced near the ceramic element 120. Therefore, the generated ions CP adhere to particles S contained in the introduced gas EGI. As a result, the particles S become positively electrified particles SC, which flow toward the gas discharge opening 60e together with the introduced gas EGI, and are discharged into the exhaust pipe EP.

Meanwhile, a predetermined potential (e.g., a positive DC potential of 100 V to 200 V) is applied from the auxiliary electrode power supply circuit 240 of the circuit section 200 to the auxiliary electrode portion 141 of the auxiliary electrode member 140 through the auxiliary potential lead wire 164 of the electric wire 163, the auxiliary potential terminal 47, and the auxiliary potential pad 147 so that the auxiliary electrode portion 141 is maintained at the auxiliary electrode potential PV3. Thus, a repulsive force directed from the auxiliary electrode portion 141 toward the inner protector 60 (collection electrode) located on the radially outward side acts on floating ions CPF, which are some of the generated ions CP and have not adhered to the particles S. As a result, the floating ions CPF are caused to adhere to various portions of the collection electrode (inner protector 60), whereby collection of the floating ions CPF by the collection electrode is assisted. Thus, the floating ions CPF can be collected reliably, and the floating ions CPF are prevented from being discharged through the gas discharge opening 60e.

In the particle detection system 1, the signal current detection circuit 230 detects the signal current Is which is a sensor signal corresponding to the amount of charge of discharged ions CPH adhering to the electrified particles SC which are discharged through the gas discharge opening 60e. As a result, the amount (concentration) of the particles S contained in the exhaust gas EG can be detected.

Notably, in the present embodiment, as shown by a broken line in FIG. 8, in the detection section 11 of the particle sensor 10, the distal end portion of the ceramic element 120 constituting the ion source 15, the inner protector 60 located around the ion source 15, and the space VO between the ion source 15 and the inner protector 60 constitute an electrification section 12 which causes the ions CP to adhere to the particles S floating in the exhaust gas EG to thereby produce electrified particles SC (see FIG. 8). Namely, in the present embodiment, the detection section 11 has the electrification section 12 including the ion source 15.

Incidentally, the particles S which are soot contained in the exhaust gas EG are likely to accumulate on and adhere to, for example, the needle-shaped electrode portion 131 of the discharge electrode member 130 of the ceramic element 120 which constitutes the ion source 15 (in particular, around the needle-shaped end portion 131ss of the needle-shaped electrode portion 131) at which corona discharge occurs (the particles S are likely to become adhering particles SA). In order to remove the adhering particles SA, it is necessary to periodically burn the adhering particles S adhering to the ceramic element 120 (the discharge portion surrounding surface 121ss of the ceramic substrate 121 and the needle-shaped end portion 131ss of the needle-shaped electrode portion 131) by heating the discharge portion surrounding surface 121ss of the ceramic substrate 121 of the ceramic element 120, which is located around the needle-shaped end portion 131ss, by the element heater 150 to a temperature at which the adhering particles SA burn (see FIG. 9).

Also, when the adhering particles SA composed of soot (particles S) adhere to the gas contact portion 101s of the first insulating spacer 100, and the insulation between the inner metallic member 20 maintained at the first potential PV1 and the outer metallic member 70 maintained at the ground potential PVE deteriorates, the detection of the small signal current Is of several μA or less; more specifically, several nA or less, involves an error which makes unable to properly detect the particles S. Therefore, it is necessary to periodically burn and remove the adhering particles SA composed of soot (particles S) adhering to the gas contact portion 101s of the first insulating spacer 100 by energizing the spacer heater 105 to thereby heat the gas contact portion 101s of the first insulating spacer 100 to a higher temperature (see FIG. 2).

Incidentally, it has been gradually revealed that, in this system 1, the particles S become less likely to adhere to the discharge portion surrounding surface 121ss of the ceramic substrate 121 and the gas contact portion 101s of the first insulating spacer 100 when the discharge portion surrounding surface 121ss and the gas contact portion 101s are heated, through heating by the element heater 150 and the spacer heater 105, to a temperature which is equal to or higher than a predetermined temperature but is lower than a temperature for burning the adhering particles SA adhering to the discharge portion surrounding surface 121ss and the gas contact portion 101s.

In view of this, in the system 1 of the present embodiment, through energization of the element heater 150 and the spacer heater 105, the discharge portion surrounding surface 121ss of the ceramic substrate 121 and the gas contact portion 101s of the first insulating spacer 100 are heated to an adhesion restraining temperature Td which is lower than a particle burning temperature Tb (at which the adhering particles SA adhering to the discharge portion surrounding surface 121ss and the gas contact portion 101s burn) but at which adhesion of the particles S to the discharge portion surrounding surface 121ss and the gas contact portion 101s is restrained as compared with the case where the element heater 150 and the spacer heater 105 are not energized.

Notably, in the present embodiment, the engine ENG is a diesel engine, and the temperature of the exhaust gas EG is about 250° C. to 300° C. Also, the particle burning temperature Tb at which the adhering particles SA such as soot burn falls within the temperature range of 650° C. to 700° C. or higher. In contrast, in the present embodiment, the adhesion restraining temperature Td is set to 350° C. which is 50° C. to 100° C. higher than the temperature of the exhaust gas EG (the actual temperature is 300° C. to 400° C. in consideration of variations of the heat generation characteristics of the element heater 150 and the spacer heater 105 and fluctuation of the temperature of the exhaust gas EG), and the discharge portion surrounding surface 121ss and the gas contact portion 101s are heated to the adhesion restraining temperature Td.

When the discharge portion surrounding surface 121ss and the gas contact portion 101s are heated to the adhesion restraining temperature Td as described above, the temperatures of the discharge portion surrounding surface 121ss and the gas contact portion 101s become higher than the temperature (250° C. to 300° C.) of the surrounding exhaust gas EG. Therefore, in the exhaust gas EG around the discharge portion surrounding surface 121ss and the gas contact portion 101s, a temperature gradient is produced such that the temperature increases toward the discharge portion surrounding surface 121ss and the gas contact portion 101s (see FIGS. 10 and 11).

Figure 10:
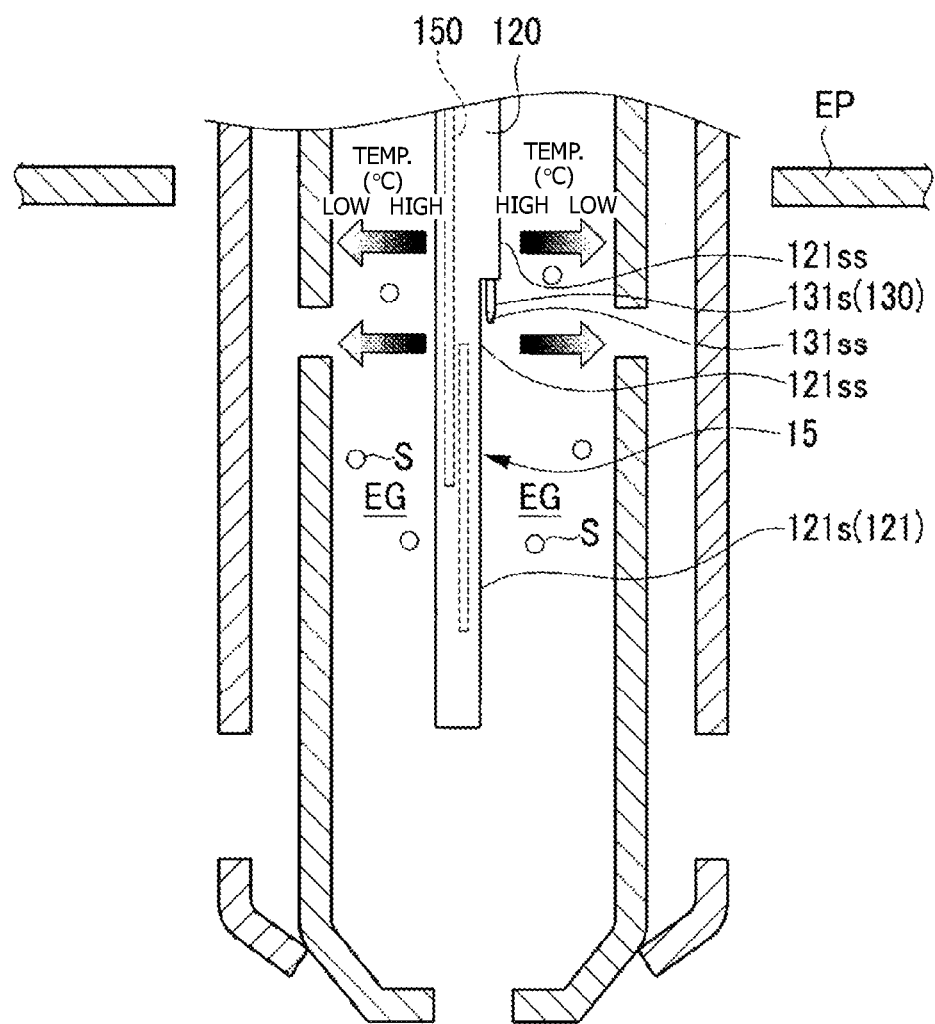
FIG. 10 is an explanatory view showing the temperature gradient produced in exhaust gas around a discharge portion surrounding surface of a ceramic substrate.
Figure 11:
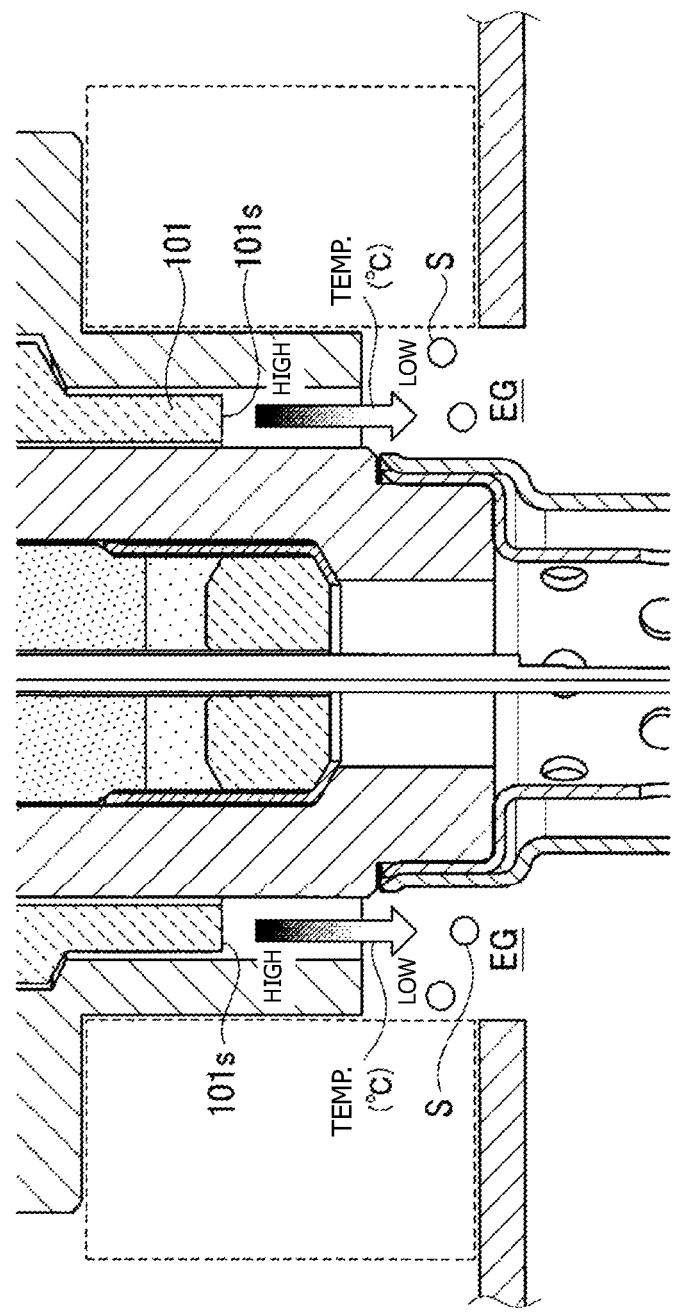
FIG. 11 is an explanatory view showing the temperature gradient produced in exhaust gas around the gas contact portion of the first insulating spacer.

When such a temperature gradient is produced in the exhaust gas EG, due to the thermal migration phenomenon, the particles S within the exhaust gas EG are likely to move from the high temperature side toward the low temperature side in accordance with the temperature gradient; i.e., in directions away from the discharge portion surrounding surface 121ss and the gas contact portion 101s (the directions of arrows in FIGS. 10 and 11). As described above, as a result of energization of the element heater 150 and the spacer heater 105 for heating the discharge portion surrounding surface 121ss and the gas contact portion 101s to the adhesion restraining temperature Td, adhesion of the particles S to the discharge portion surrounding surface 121ss and the gas contact portion 101s is restrained as compared with the case where the element heater 150 and the spacer heater 105 are not energized. Notably, both the ceramic substrate 121 and the first insulating spacer 100 are formed of alumina. Therefore, if the particle burning temperature Tb for burning the adhering particles SA is set to an excessively high temperature, due to lowering of the insulation resistances of these members, the performance of detecting the particles S may deteriorate. In order to overcome such a drawback, in the present embodiment, the particle burning temperature Tb is set to a temperature at which lowering of the insulation resistances of the ceramic substrate 121 and the first insulating spacer 100 does not substantially affect the performance of detecting the particles S.

Also, in the present embodiment, while restraining the adhesion of the particles S to the discharge portion surrounding surface 121ss and the gas contact portion 101s as described above, the adhering particles SA are periodically burned and removed by energizing the element heater 150 and the spacer heater 105. Specifically, through energization of the element heater 150 and the spacer heater 105, the discharge portion surrounding surface 121ss and the gas contact portion 101s are heated to the particle burning temperature Tb at which the adhering particles SA burn (in the present embodiment, 700° C. selected within the temperature range of 650° C. to 700° C. or higher at which the adhering particles SA burn) (the actual temperature is 650° C. to 750° C. when variations, etc. are considered), whereby the adhering particles SA are burned and removed.

Figure 12:
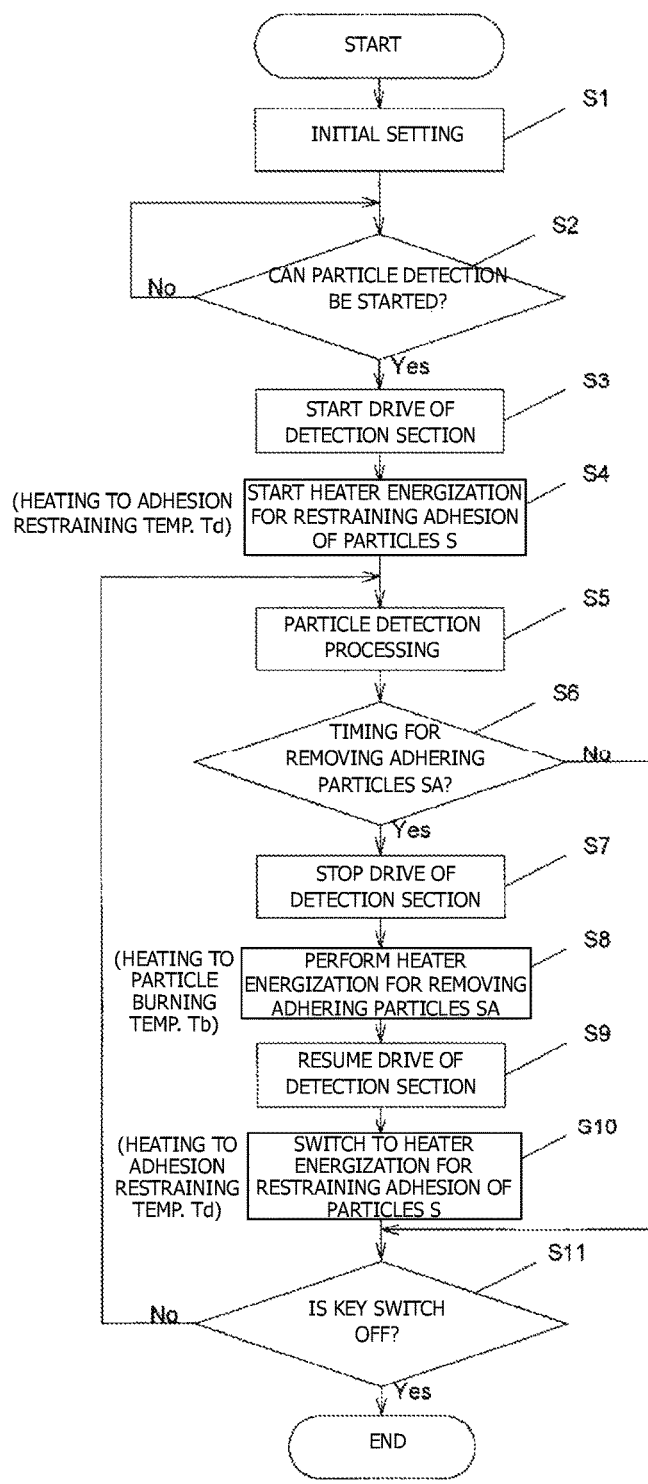
FIG. 12 is a flowchart showing operation of a microprocessor of the particle detection system according to the embodiment for performing processing for particle detection and heater energization.

Now, operation of the microprocessor 221 of the system 1 of the present embodiment which executes processing for particle detection and heater energization will be described with reference the flowchart shown in FIG. 12.

When a key switch (not shown) of the engine ENG is turned on, the present system 1 (the microprocessor 221 of the measurement control circuit 220) is started. First, in step S1, the microprocessor 221 performs initial setting necessary for particle detection and heater energization. After that, in step S2, the microprocessor 221 determines whether or not there exists an instruction signal ST (see FIG. 4) which is output from the ECU and instructs the start of the particle detection.

In the case where the instruction signal ST output from the ECU and instructing the start of the particle detection is not present (No), the microprocessor 221 repeats step S2 so as to wait for the input of the instruction signal ST output from the ECU and instructing the start of the particle detection. In the case where the instruction signal ST output from the ECU and instructing the start of the particle detection is detected (Yes), the microprocessor 221 proceeds to step S3.

In step S3, the microprocessor 221 starts the drive of the detection section 11 by applying the second potential PV2 from the ion source power supply circuit 210 to the needle-shaped electrode portion 131 (the ion source 15) of the discharge electrode member 130 and applying the auxiliary electrode potential PV3 from the auxiliary electrode power supply circuit 240 to the auxiliary electrode portion 141 of the auxiliary electrode member 140.

Further, in step S4 subsequent thereto, the microprocessor 221 starts the energization of the element heater 150 and the spacer heater 105 for restraining adhesion of the particles S. In this heater energization, the discharge portion surrounding surface 121ss of the ceramic substrate 121 and the gas contact portion 101s of the first insulating spacer 100 are heated to the adhesion restraining temperature Td (350° C. in the present embodiment) which is lower than the particle burning temperature Tb for burning the adhering particles SA but at which adhesion of the particles S to the gas contact surface is restrained as compared with the case where no heater energization is performed.

Next, in step S5, the microprocessor 221 detects the amount of the particles S contained in the exhaust gas EG (the gas under measurement) by performing a predetermined particle detection process; specifically, applying the high voltage generated at the ion source power supply circuit 210 to the ion source 15 (the discharge electrode member 130 of the ceramic element 120) to thereby produce the ions CP by means of corona discharge, and detecting the signal current Is corresponding to the amount of charge of the discharged ions CPH through use of the signal current detection circuit 230.

Next, in step S6, the microprocessor 221 determines whether or not the present point in time is a timing for removing the adhering particles SA which comes at predetermined intervals. In the case where the present point in time is the timing for removing the adhering particles SA (Yes), the microprocessor 221 proceeds to step S7. In the case where the present point in time is not the timing for removing the adhering particles SA (No), the microprocessor 221 proceeds to step S11 by skipping steps S7 to S10.

In step S7, the microprocessor 221 temporarily stops the drive of the detection section 11 for the following reason. When the adhering particles SA are removed, the insulation resistances of the ceramic substrate 121 of the ceramic element 120 and the first insulating spacer 100 lower, whereby the performance of detecting the particles S deteriorates and therefore the detection of the particles S cannot be performed.

Next, in step S8, the microprocessor 221 energizes the element heater 150 and the spacer heater 105 so as to remove the adhering particles SA. In this heater energization, the element heater 150 and the spacer heater 105 are energized over a predetermined period of time so as to heat the discharge portion surrounding surface 121ss of the ceramic substrate 121 and the gas contact portion 101s of the first insulating spacer 100 to the particle burning temperature Tb (700° C. in the present embodiment) at which the adhering particles SA burn. As a result, the adhering particles SA; i.e., the particles adhering to the discharge portion surrounding surface 121ss of the ceramic substrate 121 and the gas contact portion 101s of the first insulating spacer 100 are burned and removed.

When the energization over the predetermined period of time ends, in step S9 subsequent thereto, the microprocessor 221 resumes the drive of the detection section 11. Further, in step S10 subsequent thereto, the microprocessor 221 switches the energization of the element heater 150 and the spacer heater 105 to the heater energization for restraining adhesion of the particles S to thereby heat the discharge portion surrounding surface 121ss of the ceramic substrate 121 and the gas contact portion 101s of the first insulating spacer 100 to the adhesion restraining temperature Td (=350° C.)

Next, in step S11, the microprocessor 221 determines whether or not the key switch of the engine ENG is turned off. In the case where the key switch of the engine ENG is not turned off (No), the microprocessor 221 returns to step S5 and continues the particle detection processing. Meanwhile, in the case where the key switch of the engine ENG is turned off (Yes), the microprocessor 221 ends the processing for particle detection and heater energization.

In the present embodiment, the ceramic substrate 121 of the ceramic element 120 corresponds to the insulating member, and the first insulating spacer 100 corresponds to the insulating member and the insulating spacer. Also, the element heater 150 provided in the ceramic element 120 and the spacer heater 105 provided in the first insulating spacer 100 correspond to the heater section. Further, the gas contact surface 121s (including the discharge portion surrounding surface 121ss) of the ceramic substrate 121 and the gas contact portion 101s of the first insulating spacer 100 correspond to the gas contact surface.

Also, the second heater energization circuit 225 and the first heater energization circuit 223 of the measurement control circuit 220 and the microprocessor 221 which executes step S4 and step S10 correspond to the adhesion restraining energization means.

Further, the second heater energization circuit 225 and the first heater energization circuit 223 of the measurement control circuit 220 and the microprocessor 221 which executes step S8 correspond to the burning removal energization means.

As described above, in the system 1 of the present embodiment, through energization of the element heater 150 and the spacer heater 105 (the heater section) by the adhesion restraining energization means (step S4 and step S10), the discharge portion surrounding surface 121ss of the ceramic substrate 121 and the gas contact portion 101s of the first insulating spacer 100 are heated to the adhesion restraining temperature Td (=350° C.). As a result, due to the thermal migration phenomenon, the particles S within the exhaust gas EG become more likely to move in directions away from the discharge portion surrounding surface 121ss of the ceramic substrate 121 and the gas contact portion 101s of the first insulating spacer 100. Thus, adhesion of the particles S to the discharge portion surrounding surface 121ss and the gas contact portion 101s is restrained as compared with the case where the element heater 150 and the spacer heater 105 are not energized.

Further, in the system 1 of the present embodiment, through energization of the heater section by the burning removal energization means (step S8), the discharge portion surrounding surface 121ss of the ceramic substrate 121 and the gas contact portion 101s of the first insulating spacer 100 are heated to the particle burning temperature Tb (=700° C.), whereby the adhering particles SA; i.e., the particles adhering to the discharge portion surrounding surface 121ss and the gas contact portion 101s are burned and removed. Thus, adhesion of the particles S to the discharge portion surrounding surface 121ss and the gas contact portion 101s can be restrained by energizing the heater section by the adhesion restraining energization means (step S4 and step S10). In addition, when the adhering particles SA are present; i.e., when the particles have adhered to the discharge portion surrounding surface 121ss and the gas contact portion 101s, the adhering particles SA can be burned and removed by energizing the heater section by the burning removal energization means (step S8). Also, the frequency at which the adhering particles SA are burned and removed by the burning removal energization means (step S8) can be decreased as compared with the case where the adhesion restraining energization means (step S4 and step S10) is not provided.

Further, in the system 1 of the present embodiment, the discharge portion surrounding surface 121ss of the ceramic substrate 121 (the insulating member) of the ceramic element 120, which substrate covers the discharge electrode member 130, is heated by the element heater 150 (the heater section). As a result, it is possible to restrain adhesion of the particles S to the discharge portion surrounding surface 121ss of the ceramic substrate 121 and the needle-shaped end portion 131ss (discharge portion) of the needle-shaped electrode portion 131. Therefore, it is possible to properly produce gaseous discharge at the ion source 15 and properly detect the particles S.

Further, in the system 1 of the present embodiment, the gas contact portion 101s (the gas contact surface) of the first insulating spacer 100 (the insulating member, the insulating spacer) intervening between the inner metallic member 20 maintained at the first potential PV1 and the outer metallic member 70 maintained at the ground potential PVE is heated by the spacer heater 105 (the heater section).

As a result, it is possible to suppress the leak current flowing between the first potential PV1 and the ground potential PVE. Thus, it is possible to suppress lowering of the accuracy in detecting the signal current Is to thereby allow proper detection of the particles S.

Although the present invention has been described on the basis of the embodiment thereof, the present invention is not limited to the above-described embodiment and can be applied through proper modification without departing from the gist of the invention.

For example, in the embodiment, the present invention is applied to a particle detection system in which the detection section 11 exposed to the exhaust gas EG (the gas under measurement) has the electrification section 12 including the ion source 15 for producing the ions CP by means of gaseous discharge. However, the detection section of the particle sensor is not limited thereto. For example, the present invention may be applied to a particle detection system including a particle sensor in which an electrification section for causing particles to adhere to the surface of an electrode and electrifying the particles S so that the particles S become electrified particles SC through application of a high voltage to the electrode is provided in the detection section of the particle sensor (see Patent Documents 2 and 3). In this case, an example of the heater section is a heater for heating the insulating member which insulates the electrodes of the electrification section to which particles adhere.

Also, in the embodiment, the ceramic substrate 121 and the first insulating spacer 100 are formed of alumina and the engine ENG is a diesel engine. Therefore, the adhesion restraining temperature Td is set to 350° C. However, the temperature of the exhaust gas EG (the gas under measurement) changes depending on the type of the engine, fuel, etc., and the temperature at which the insulation resistance of the insulating member drops changes depending on the material used as an insulating material for the insulating member. Therefore, it is good to set the adhesion restraining temperature Td to a proper temperature in consideration of the temperature of the gas under measurement and the material of the insulating member.

DESCRIPTION OF REFERENCE NUMERALS

1: particle detection system
10: particle sensor
11: detection section
12: electrification section
15: ion source
20: inner metallic member
25: gas introduction pipe
30: metallic shell
40: inner tube
50: inner-tube metal connection member
60: inner protector
60e: gas discharge opening
65: outer protector
65c: gas introduction hole
70: outer metallic member
80: mounting metallic member
90: outer tube
100: first insulating spacer (insulating member, insulating spacer)
101: spacer distal end portion
101s: gas contact portion (gas contact surface)
105: spacer heater (heater section)
120: ceramic element
121: ceramic substrate (insulating member)
121s: gas contact surface
121ss: discharge portion surrounding surface
130: discharge electrode member
140: auxiliary electrode member
150: element heater (heater section)
200: circuit section
210: ion source power supply circuit
220: measurement control circuit
221: microprocessor
223: first heater energization circuit (adhesion restraining energization means, burning removal energization means)
225: second heater energization circuit (adhesion restraining energization means, burning removal energization means)
230: signal current detection circuit
240: auxiliary electrode power supply circuit
AM: vehicle
ENG: engine
EP: exhaust pipe (gas flow pipe)
EG: exhaust gas
EGI: introduced gas
S: particle
ECU: engine control unit
PVE: ground potential
PV1: first potential
SA: adhering particle
Tb: particle burning temperature
Td: adhesion restraining temperature
S4, S10: adhesion restraining energization means
S8: burning removal energization means

The invention claimed is:

1. A particle detection system comprising a particle sensor which has a detection section to be exposed to a gas under measurement and which detects particles contained in the gas under measurement, wherein the particle sensor includes:

an insulating member formed of an insulating material having a gas contact surface which comes into contact with the gas under measurement and whose insulating performance deteriorates when the particles contained in the gas under measurement adhere thereto, to thereby lower a performance of detecting the particles by the detection section, and a heater section which generates heat upon energization so as to heat at least a portion of the gas contact surface of the insulating member; and the particle detection system is configured to perform an adhesion restraining energization function to heat the gas contact surface, by energization of the heater section, to an adhesion restraining temperature which is higher than a temperature of the gas under measurement and lower than a temperature at which the particles will burn but at which adhesion of the particles to the gas contact surface is restrained as compared with the case where the heater section is not energized, the particle detection system is configured to perform a burning removal energization function to heat the gas contact surface to the particle burning temperature through energization of the heater section to thereby burn and remove the adhering particles, and the particle detection system is configured to maintain the gas contact surface at the adhesion restraining temperature and to periodically perform the burning removal energization function at predetermined times.

2. A particle detection system according to claim 1, wherein the detection section includes an electrification section which includes an ion source for producing ions by means of gaseous discharge and which causes the produced ions to adhere to the particles floating within the gas under measurement to thereby electrify the particles so that the particles become electrified particles;

the ion source has a discharge electrode member including a discharge portion at which the gaseous discharge occurs;

the insulating member covers the discharge electrode member while exposing the discharge portion and has a discharge portion surrounding surface which is the gas contact surface and is located around the discharge portion; and the heater section heats the discharge portion surrounding surface of the insulating member.

3. A particle detection system according to claim 1, wherein the particle sensor is attached to a gas flow pipe through which the gas under measurement flows and which gas flow pipe is maintained at a ground potential so that the detection section faces an interior of the gas flow pipe;

the particle sensor includes an inner metallic member which includes a gas introduction pipe for introducing the gas under measurement into the particle sensor, which inner metallic member is maintained at a first potential different from the ground potential and which forms a portion of the detection section, and a tubular outer metallic member which surrounds a radially outer circumference of the inner metallic member and which is attached to the gas flow pipe to thereby be maintained at the ground potential;

the insulating member is an insulating spacer which intervenes between the inner metallic member and the outer metallic member so as to electrically insulate the metallic members from each other while separating the metallic members from each other; and the heater section heats the gas contact surface of the insulating spacer.

4. A particle detection system according to claim 1, wherein the particles comprise soot particles.

5. A particle detection system according to claim 1, wherein the particles comprise soot particles and the gas contact surface is heated to the adhesion restraining temperature which is lower than the temperature at which the soot particles will burn and higher than a temperature of the gas under measurement to which the detection system is exposed such that adhesion of the soot particles to the gas contact surface is restrained as compared with the case where the heater section is not energized.

* * * * *